(12) United States Patent
Breindel et al.

(10) Patent No.: US 12,048,541 B2
(45) Date of Patent: Jul. 30, 2024

(54) BLOOD SEQUESTRATION DEVICE AND METHOD

(71) Applicant: Smiths Medical ASD, Inc., Plymouth, MN (US)

(72) Inventors: Jay T. Breindel, Branford, CT (US); Harsh D. Chheda, Cheshire, CT (US)

(73) Assignee: Smiths Medical ASD, Inc., Plymouth, MN (US)

( * ) Notice: Subject to any disclaimer, the term of this patent is extended or adjusted under 35 U.S.C. 154(b) by 0 days.

(21) Appl. No.: 17/937,072

(22) Filed: Sep. 30, 2022

(65) Prior Publication Data
US 2023/0023330 A1 Jan. 26, 2023

Related U.S. Application Data

(60) Division of application No. 16/451,445, filed on Jun. 25, 2019, now Pat. No. 11,490,840, which is a
(Continued)

(51) Int. Cl.
*A61B 5/15* (2006.01)
*A61B 5/153* (2006.01)

(52) U.S. Cl.
CPC .. *A61B 5/150213* (2013.01); *A61B 5/150251* (2013.01); *A61B 5/15003* (2013.01); *A61B 5/150221* (2013.01); *A61B 5/153* (2013.01)

(58) Field of Classification Search
CPC ........ A61B 5/150213; A61B 5/150251; A61B 5/15003; A61B 5/150221; A61B 5/15074;
(Continued)

(56) References Cited

U.S. PATENT DOCUMENTS 2,642,065 A 6/1953 Mario et al.
3,270,743 A 9/1966 Pierre et al.
(Continued)

FOREIGN PATENT DOCUMENTS

CN 1427731 A 7/2003
CN 102387831 A 3/2012
(Continued)

OTHER PUBLICATIONS

Application and File History for U.S. Appl. No. 15/012,013, filed Feb. 1, 2016, Inventors Akcay, et al.
(Continued)

*Primary Examiner* — Yi-Shan Yang
*Assistant Examiner* — Om Patel
(74) *Attorney, Agent, or Firm* — Husch Blackwell LLP

(57) ABSTRACT

A blood sequestration device configured to isolate an initial, potentially contaminated portion of blood from the flow of blood of a patient, prior to directing the flow of blood to an outlet port where the blood can be accessed. The blood sequestration device including a body member having an interior wall defining a fluid conduit having a distal portion, a first proximal portion, and a second proximal portion, wherein the first proximal portion defines a sequestration chamber configured to isolate an initial portion of blood of a flow of blood, a vent path configured to enable the escape of gas initially trapped within the sequestration chamber.

19 Claims, 12 Drawing Sheets

Related U.S. Application Data continuation of application No. 16/434,284, filed on Jun. 7, 2019, now Pat. No. 11,857,320.

(60) Provisional application No. 62/682,362, filed on Jun. 8, 2018.

(58) Field of Classification Search
CPC ........ A61B 5/150648; A61B 5/150992; A61B 5/153; A61B 5/150389; A61B 5/150908
See application file for complete search history.

(56) References Cited

U.S. PATENT DOCUMENTS

| | | |
|---|---|---|
| 3,298,789 A | 1/1967 | Mast |
| 3,392,862 A | 7/1968 | Faulstich |
| D217,702 S | 5/1970 | Volk et al. |
| 3,680,559 A | 8/1972 | Gorbahn |
| 3,692,490 A | 9/1972 | Hall et al. |
| 3,753,432 A * | 8/1973 | Guerra ................... A61B 5/154 600/577 |
| 3,977,401 A | 8/1976 | Pike |
| D257,885 S | 1/1981 | Kulle |
| 4,243,035 A | 1/1981 | Barrett |
| 4,317,445 A | 3/1982 | Robinson |
| 4,352,354 A | 10/1982 | Ujihara |
| D283,921 S | 5/1986 | Dyak |
| D289,687 S | 5/1987 | Boyle et al. |
| D298,171 S | 10/1988 | McFarlane |
| 4,799,926 A | 1/1989 | Haber |
| 4,842,591 A | 6/1989 | Luther |
| 4,863,432 A | 9/1989 | Kvalo |
| 4,954,130 A | 9/1990 | Edwards |
| 4,994,034 A | 2/1991 | Botich et al. |
| 5,000,740 A | 3/1991 | Ducharme et al. |
| 5,007,901 A | 4/1991 | Shields |
| 5,053,014 A | 10/1991 | Van Heugten |
| D326,154 S | 5/1992 | Deguchi et al. |
| 5,114,678 A | 5/1992 | Crawford et al. |
| 5,149,328 A | 9/1992 | Zaha |
| 5,190,521 A | 3/1993 | Hubbard et al. |
| 5,195,983 A | 3/1993 | Boese |
| 5,201,324 A | 4/1993 | Swierczek |
| 5,215,528 A | 6/1993 | Purdy et al. |
| 5,279,590 A | 1/1994 | Sinko et al. |
| 5,312,367 A | 5/1994 | Nathan |
| 5,322,518 A | 6/1994 | Schneider et al. |
| 5,330,439 A | 7/1994 | Jackson |
| 5,342,315 A | 8/1994 | Rowe et al. |
| 5,368,029 A | 11/1994 | Holcombe et al. |
| 5,401,250 A | 3/1995 | Shields |
| 5,438,984 A | 8/1995 | Schoendorfer |
| 5,441,048 A | 8/1995 | Schoendorfer |
| 5,465,713 A | 11/1995 | Schoendorfer |
| 5,498,247 A | 3/1996 | Brimhall |
| 5,505,694 A | 4/1996 | Hubbard et al. |
| 5,512,052 A | 4/1996 | Jesch |
| 5,531,699 A | 7/1996 | Tomba et al. |
| 5,531,720 A | 7/1996 | Atkins |
| 5,558,641 A | 9/1996 | Glantz et al. |
| 5,599,310 A | 2/1997 | Bogert |
| 5,638,815 A | 6/1997 | Schoendorfer |
| 5,676,346 A | 10/1997 | Leinsing |
| 5,676,656 A | 10/1997 | Brimhall |
| 5,676,658 A | 10/1997 | Erskine |
| 5,685,855 A | 11/1997 | Erskine |
| 5,685,866 A | 11/1997 | Lopez |
| 5,694,978 A | 12/1997 | Heilmann et al. |
| 5,697,914 A | 12/1997 | Brimhall |
| 5,700,250 A | 12/1997 | Erskine |
| 5,713,874 A | 2/1998 | Ferber |
| 5,713,876 A | 2/1998 | Bogert et al. |
| 5,718,688 A | 2/1998 | Wozencroft |
| 5,738,664 A | 4/1998 | Erskine et al. |
| 5,743,891 A | 4/1998 | Tolkoff et al. |
| 5,755,709 A | 5/1998 | Cuppy |
| D395,501 S | 6/1998 | Erskine et al. |
| 5,772,636 A | 6/1998 | Brimhall et al. |
| 5,795,339 A | 8/1998 | Erskine |
| 5,810,780 A | 9/1998 | Brimhall et al. |
| 5,817,011 A | 10/1998 | Schoendorfer |
| 5,817,012 A | 10/1998 | Schoendorfer |
| 5,817,069 A | 10/1998 | Arnett |
| 5,853,339 A | 12/1998 | Scerbo |
| 5,853,393 A | 12/1998 | Bogert |
| 5,858,002 A | 1/1999 | Jesch |
| 5,873,862 A | 2/1999 | Lopez |
| 5,879,334 A | 3/1999 | Brimhall |
| 5,885,253 A | 3/1999 | Liu |
| D408,530 S | 4/1999 | Eliasen et al. |
| 5,897,497 A | 4/1999 | Fernandez |
| 5,911,705 A | 6/1999 | Howell |
| 5,919,356 A | 7/1999 | Hood |
| 5,928,204 A | 7/1999 | Lopez |
| 5,935,109 A | 8/1999 | Donnan |
| 5,935,110 A | 8/1999 | Brimhall |
| 5,944,662 A | 8/1999 | Schoendorfer |
| 5,951,515 A | 9/1999 | Osterlind |
| 5,989,229 A | 11/1999 | Chiappetta |
| 5,997,524 A | 12/1999 | Burbank et al. |
| 6,004,278 A * | 12/1999 | Botich ............. A61B 5/150656 600/576 |
| 6,004,294 A | 12/1999 | Brimhall et al. |
| 6,056,726 A | 5/2000 | Isaacson |
| 6,077,244 A | 6/2000 | Botich et al. |
| 6,117,108 A | 9/2000 | Woehr et al. |
| 6,126,641 A | 10/2000 | Shields |
| 6,213,978 B1 | 4/2001 | Voyten |
| 6,221,047 B1 | 4/2001 | Greene et al. |
| 6,228,060 B1 | 5/2001 | Howell |
| 6,245,048 B1 | 6/2001 | Fangrow, Jr. et al. |
| 6,287,278 B1 | 9/2001 | Woehr et al. |
| D448,844 S | 10/2001 | Reis |
| 6,379,332 B1 | 4/2002 | Van Landuyt |
| 6,379,333 B1 | 4/2002 | Brimhall et al. |
| D459,802 S | 7/2002 | Cindrich |
| 6,461,362 B1 | 10/2002 | Halseth et al. |
| 6,506,181 B2 | 1/2003 | Meng et al. |
| 6,547,762 B1 | 4/2003 | Botich et al. |
| 6,572,592 B1 | 6/2003 | Lopez |
| 6,585,703 B1 | 7/2003 | Kassel et al. |
| 6,595,955 B2 | 7/2003 | Ferguson et al. |
| 6,603,987 B2 | 8/2003 | Whitson |
| 6,616,630 B1 | 9/2003 | Woehr et al. |
| 6,638,252 B2 | 10/2003 | Moulton et al. |
| 6,652,490 B2 | 11/2003 | Howell |
| 6,663,592 B2 | 12/2003 | Rhad et al. |
| 6,669,673 B2 | 12/2003 | Lopez |
| 6,682,509 B2 | 1/2004 | Lopez |
| 6,709,419 B2 | 3/2004 | Woehr |
| 6,719,726 B2 | 4/2004 | Meng et al. |
| 6,719,727 B2 | 4/2004 | Brimhall et al. |
| 6,749,588 B1 | 6/2004 | Howell et al. |
| 6,796,962 B2 | 9/2004 | Ferguson et al. |
| 6,840,912 B2 | 1/2005 | Kloepfer et al. |
| 6,872,193 B2 | 3/2005 | Shaw et al. |
| 6,902,546 B2 | 6/2005 | Ferguson |
| 6,914,212 B2 | 7/2005 | Adams |
| 6,916,310 B2 | 7/2005 | Sommerich |
| 6,953,448 B2 | 10/2005 | Moulton et al. |
| 6,972,002 B2 | 12/2005 | Thorne |
| 6,979,323 B2 | 12/2005 | Rogers et al. |
| 6,984,213 B2 | 1/2006 | Horner et al. |
| 6,986,760 B2 | 1/2006 | Giambattista et al. |
| 7,002,098 B2 | 2/2006 | Adams |
| 7,004,927 B2 | 2/2006 | Ferguson et al. |
| 7,008,402 B2 | 3/2006 | Ferguson et al. |
| 7,106,269 B1 | 9/2006 | Tonn |
| 7,125,396 B2 | 10/2006 | Leinsing et al. |
| 7,125,397 B2 | 10/2006 | Woehr et al. |
| 7,179,244 B2 | 2/2007 | Smith et al. |
| 7,186,239 B2 | 3/2007 | Woehr |
| 7,214,211 B2 | 5/2007 | Woehr et al. |
| 7,226,434 B2 | 6/2007 | Carlyon et al. |

(56) References Cited

U.S. PATENT DOCUMENTS

| | | |
|---|---|---|
| 7,255,685 B2 | 8/2007 | Pressly, Sr. et al. |
| 7,264,613 B2 | 9/2007 | Woehr et al. |
| 7,291,130 B2 | 11/2007 | McGurk |
| 7,314,462 B2 | 1/2008 | O'Reagan et al. |
| 7,331,940 B2 | 2/2008 | Sommerich |
| 7,341,573 B2 | 3/2008 | Ferguson et al. |
| 7,357,784 B2 | 4/2008 | Ferguson |
| 7,390,317 B2 | 6/2008 | Taylor et al. |
| 7,393,345 B2 | 7/2008 | Yang |
| 7,413,562 B2 | 8/2008 | Ferguson et al. |
| 7,458,954 B2 | 12/2008 | Ferguson et al. |
| 7,470,254 B2 | 12/2008 | Basta et al. |
| 7,507,222 B2 | 3/2009 | Cindrich et al. |
| 7,604,616 B2 | 10/2009 | Thoresen et al. |
| 7,608,057 B2 | 10/2009 | Woehr et al. |
| 7,611,485 B2 | 11/2009 | Ferguson |
| 7,611,487 B2 | 11/2009 | Woehr et al. |
| 7,611,499 B2 | 11/2009 | Woehr et al. |
| 7,618,395 B2 | 11/2009 | Ferguson |
| 7,625,360 B2 | 12/2009 | Woehr et al. |
| 7,635,352 B2 | 12/2009 | Adams |
| D608,886 S | 1/2010 | Rueckert et al. |
| 7,654,988 B2 | 2/2010 | Moulton et al. |
| 7,658,725 B2 | 2/2010 | Bialecki et al. |
| 7,662,110 B2 | 2/2010 | Flaherty |
| D612,044 S | 3/2010 | Scheibe |
| 7,670,317 B2 | 3/2010 | Cindrich et al. |
| 7,678,076 B2 | 3/2010 | Crawford |
| 7,691,088 B2 | 4/2010 | Howell |
| 7,691,093 B2 | 4/2010 | Brimhall |
| 7,713,248 B2 | 5/2010 | Lopez |
| 7,713,257 B2 | 5/2010 | Brimhall et al. |
| 7,722,569 B2 | 5/2010 | Soderholm et al. |
| 7,731,691 B2 | 6/2010 | Cote et al. |
| 7,731,692 B2 | 6/2010 | Moos et al. |
| 7,736,332 B2 | 6/2010 | Carlyon et al. |
| 7,736,336 B2 | 6/2010 | Plishka et al. |
| 7,736,342 B2 | 6/2010 | Abriles et al. |
| 7,763,006 B2 | 7/2010 | Tennican |
| 7,766,897 B2 | 8/2010 | Ramsey et al. |
| 7,785,299 B2 | 8/2010 | Crawford et al. |
| 7,798,994 B2 | 9/2010 | Brimhall |
| 7,799,010 B2 | 9/2010 | Tennican |
| 7,806,849 B2 | 10/2010 | Woehr |
| 7,806,869 B2 | 10/2010 | Nilsson et al. |
| 7,828,774 B2 | 11/2010 | Harding et al. |
| 7,871,430 B2 | 1/2011 | Pavcnik et al. |
| D634,421 S | 3/2011 | El-Gad et al. |
| 7,901,364 B2 | 3/2011 | Kloepfer et al. |
| 7,914,488 B2 | 3/2011 | Dickerson |
| 7,922,701 B2 | 4/2011 | Buchman |
| D638,934 S | 5/2011 | Kimmel |
| 7,935,080 B2 | 5/2011 | Howell et al. |
| 7,972,313 B2 | 7/2011 | Woehr et al. |
| 7,972,322 B2 | 7/2011 | Tennican |
| 7,976,502 B2 | 7/2011 | Baid |
| D642,596 S | 8/2011 | Hinklin et al. |
| 7,988,664 B2 | 8/2011 | Fiser et al. |
| D645,962 S | 9/2011 | Shaw et al. |
| 8,029,472 B2 | 10/2011 | Leinsing et al. |
| 8,048,061 B2 | 11/2011 | Kurth et al. |
| 8,057,443 B2 | 11/2011 | McNeil |
| 8,062,261 B2 | 11/2011 | Adams |
| 8,062,262 B2 | 11/2011 | Christensen et al. |
| 8,066,669 B2 | 11/2011 | Christensen et al. |
| 8,066,670 B2 | 11/2011 | Cluff et al. |
| 8,066,675 B2 | 11/2011 | Cindrich et al. |
| 8,070,725 B2 | 12/2011 | Christensen |
| 8,096,973 B2 | 1/2012 | Snow et al. |
| 8,100,858 B2 | 1/2012 | Woehr et al. |
| D655,406 S | 3/2012 | Ma et al. |
| 8,147,455 B2 | 4/2012 | Butts et al. |
| 8,162,899 B2 | 4/2012 | Tennican |
| 8,162,904 B2 | 4/2012 | Takano et al. |
| 8,163,237 B2 | 4/2012 | Crawford et al. |
| D660,420 S | 5/2012 | Shaw et al. |
| 8,167,851 B2 | 5/2012 | Sen |
| 8,211,070 B2 | 7/2012 | Woehr et al. |
| 8,216,188 B2 | 7/2012 | Millerd et al. |
| 8,249,681 B2 | 8/2012 | Rabinovitz |
| 8,257,313 B2 | 9/2012 | McKinnon et al. |
| 8,257,322 B2 | 9/2012 | Koehler et al. |
| 8,262,643 B2 | 9/2012 | Tennican |
| 8,273,056 B2 | 9/2012 | Kuracina et al. |
| 8,292,852 B2 | 10/2012 | Mulholland et al. |
| 8,308,691 B2 | 11/2012 | Woehr et al. |
| 8,328,769 B2 | 12/2012 | Dikeman et al. |
| 8,337,461 B2 | 12/2012 | Burkholz |
| 8,348,893 B2 | 1/2013 | Carlyon |
| 8,357,119 B2 | 1/2013 | Stout et al. |
| 8,357,121 B2 | 1/2013 | Burkholz |
| 8,361,020 B2 | 1/2013 | Stout |
| 8,366,684 B2 | 2/2013 | Harding |
| 8,376,994 B2 | 2/2013 | Woehr et al. |
| 8,377,040 B2 | 2/2013 | Burkholz et al. |
| 8,382,718 B2 | 2/2013 | Woehr |
| 8,382,721 B2 | 2/2013 | Woehr et al. |
| 8,383,044 B2 | 2/2013 | Davis et al. |
| 8,394,064 B2 | 3/2013 | Baid |
| 8,403,822 B2 | 3/2013 | Benson et al. |
| 8,412,300 B2 | 4/2013 | Sonderegger |
| 8,414,539 B1 | 4/2013 | Kuracina et al. |
| 8,419,687 B2 | 4/2013 | Moos et al. |
| 8,419,688 B2 | 4/2013 | Woehr et al. |
| 8,444,605 B2 | 5/2013 | Kuracina et al. |
| 8,460,247 B2 | 6/2013 | Woehr et al. |
| 8,460,249 B2 | 6/2013 | Woehr |
| 8,469,928 B2 | 6/2013 | Stout et al. |
| D686,316 S | 7/2013 | Baid |
| 8,474,300 B2 | 7/2013 | McKinnon et al. |
| 8,480,968 B2 | 7/2013 | Lynn |
| 8,486,024 B2 | 7/2013 | Steube |
| 8,496,623 B2 | 7/2013 | Burkholz |
| 8,506,528 B2 | 8/2013 | Fiser et al. |
| 8,523,809 B2 | 9/2013 | Moos et al. |
| 8,529,515 B2 | 9/2013 | Woehr et al. |
| 8,535,257 B1 | 9/2013 | Zelten et al. |
| 8,540,728 B2 | 9/2013 | Woehr et al. |
| 8,545,454 B2 | 10/2013 | Kuracina et al. |
| 8,568,372 B2 | 10/2013 | Woehr et al. |
| 8,574,203 B2 | 11/2013 | Stout et al. |
| 8,585,651 B2 | 11/2013 | Asai |
| 8,591,467 B2 | 11/2013 | Walker et al. |
| 8,591,468 B2 | 11/2013 | Woehr et al. |
| 8,591,476 B2 | 11/2013 | Winsor et al. |
| 8,597,249 B2 | 12/2013 | Woehr et al. |
| 8,597,252 B2 | 12/2013 | Burkholz et al. |
| 8,641,675 B2 | 2/2014 | Stout et al. |
| 8,641,676 B2 | 2/2014 | Butts et al. |
| 8,647,294 B2 | 2/2014 | Bonnette et al. |
| 8,647,313 B2 | 2/2014 | Woehr et al. |
| 8,679,063 B2 | 3/2014 | Stout et al. |
| 8,690,833 B2 | 4/2014 | Belson |
| 8,702,658 B2 | 4/2014 | Spearman |
| 8,721,546 B2 | 5/2014 | Belson |
| 8,728,038 B2 | 5/2014 | Spearman |
| 8,740,850 B2 | 6/2014 | Leinsing et al. |
| 8,747,333 B2 | 6/2014 | Burkholz |
| D709,188 S | 7/2014 | Guala |
| 8,764,711 B2 | 7/2014 | Kuracina et al. |
| 8,784,387 B2 | 7/2014 | Woehr |
| 8,814,833 B2 | 8/2014 | Farrell et al. |
| 8,821,439 B2 | 9/2014 | Kuracina et al. |
| 8,827,965 B2 | 9/2014 | Woehr et al. |
| 8,834,422 B2 | 9/2014 | Walker et al. |
| 8,845,584 B2 | 9/2014 | Ferguson et al. |
| D715,423 S | 10/2014 | Rogers |
| 8,864,714 B2 | 10/2014 | Harding et al. |
| 8,870,825 B2 | 10/2014 | Grandolfo |
| 8,915,883 B2 | 12/2014 | Baid |
| 8,926,563 B2 | 1/2015 | Steube |
| 8,932,259 B2 | 1/2015 | Stout et al. |
| 8,936,575 B2 | 1/2015 | Moulton |
| 8,956,328 B2 | 2/2015 | Antonucci |

(56) References Cited

U.S. PATENT DOCUMENTS

| | | |
|---|---|---|
| 8,986,227 B2 | 3/2015 | Belson |
| D732,160 S | 6/2015 | Du |
| D732,166 S | 6/2015 | Lualdi |
| 9,089,671 B2 | 7/2015 | Stout et al. |
| 9,089,673 B2 | 7/2015 | Fiser et al. |
| 9,108,021 B2 | 8/2015 | Hyer et al. |
| 9,114,231 B2 | 8/2015 | Woehr et al. |
| 9,138,564 B2 | 9/2015 | Morrissey et al. |
| 9,180,277 B2 | 11/2015 | Erskine |
| 9,241,663 B2 | 1/2016 | Jena et al. |
| 9,393,382 B2 | 7/2016 | Heck |
| 9,399,116 B2 | 7/2016 | Goral et al. |
| 9,545,495 B2 | 1/2017 | Goral et al. |
| D787,665 S | 5/2017 | Wu |
| 9,808,580 B2 | 11/2017 | Elmen |
| D806,862 S | 1/2018 | Semmann |
| D808,013 S | 1/2018 | Chheda et al. |
| 10,028,691 B2 | 7/2018 | Goral et al. |
| D844,774 S | 4/2019 | Akcay et al. |
| 10,548,522 B2 | 2/2020 | Akcay et al. |
| 10,675,440 B2 | 6/2020 | Abitabilo et al. |
| D893,711 S | 8/2020 | Chheda et al. |
| 2002/0133122 A1 | 9/2002 | Giambattista et al. |
| 2002/0165496 A1 | 11/2002 | Thompson |
| 2003/0083621 A1 | 5/2003 | Shaw et al. |
| 2003/0171721 A1 | 9/2003 | Enomoto et al. |
| 2003/0199827 A1 | 10/2003 | Thorne |
| 2004/0068202 A1 | 4/2004 | Hansson et al. |
| 2004/0116830 A1 | 6/2004 | Trudeau et al. |
| 2004/0133090 A1 | 7/2004 | Dostoinov et al. |
| 2004/0193118 A1 | 9/2004 | Bergeron |
| 2004/0225260 A1 | 11/2004 | Villa et al. |
| 2005/0043709 A1 | 2/2005 | Brimhall et al. |
| 2005/0182363 A1 | 8/2005 | Kulli |
| 2005/0273019 A1 | 12/2005 | Conway et al. |
| 2005/0273057 A1 | 12/2005 | Popov |
| 2006/0149189 A1 | 7/2006 | Diamond et al. |
| 2007/0060905 A1 | 3/2007 | Howell |
| 2007/0112305 A1 | 5/2007 | Brimhall |
| 2007/0167917 A1 | 7/2007 | Lee |
| 2007/0191771 A1 | 8/2007 | Moyer |
| 2007/0191776 A1 | 8/2007 | Bialecki et al. |
| 2007/0196414 A1 | 8/2007 | Hammarsten et al. |
| 2007/0250037 A1 | 10/2007 | Brimhall et al. |
| 2008/0097330 A1 | 4/2008 | King et al. |
| 2008/0097344 A1 | 4/2008 | McKinnon et al. |
| 2008/0146896 A1 | 6/2008 | Rabinowitz et al. |
| 2008/0264979 A1 | 10/2008 | Nijland et al. |
| 2008/0300543 A1 | 12/2008 | Abriles et al. |
| 2008/0319387 A1 | 12/2008 | Amisar et al. |
| 2009/0088696 A1 | 4/2009 | Harding et al. |
| 2009/0227953 A1 | 9/2009 | Tan et al. |
| 2009/0234246 A1 | 9/2009 | Usui |
| 2010/0076384 A1 | 3/2010 | Trask et al. |
| 2010/0191189 A1 | 7/2010 | Harding et al. |
| 2010/0280463 A1 | 11/2010 | Murayama et al. |
| 2010/0331726 A1 | 12/2010 | Steube et al. |
| 2011/0054440 A1 | 3/2011 | Lewis |
| 2011/0106014 A1 | 5/2011 | Helm, Jr. |
| 2011/0160671 A1 | 6/2011 | Tanabe et al. |
| 2011/0301553 A1 | 12/2011 | Goral et al. |
| 2011/0313391 A1 | 12/2011 | Knapp, II et al. |
| 2011/0319825 A1 | 12/2011 | Goral et al. |
| 2012/0004622 A1 | 1/2012 | Leeflang et al. |
| 2012/0016265 A1 | 1/2012 | Peterson et al. |
| 2012/0016266 A1 | 1/2012 | Burkholz |
| 2012/0016318 A1 | 1/2012 | Hoang et al. |
| 2012/0035552 A1 | 2/2012 | Woehr |
| 2012/0101440 A1 | 4/2012 | Kamen et al. |
| 2012/0197204 A1 | 8/2012 | Helm, Jr. |
| 2012/0226239 A1 | 9/2012 | Green |
| 2012/0232489 A1 | 9/2012 | Helm, Jr. |
| 2012/0265155 A1 | 10/2012 | Baez |
| 2012/0277630 A1 | 11/2012 | Devgon |
| 2012/0302968 A1 | 11/2012 | Tennican |
| 2012/0302970 A1 | 11/2012 | Tennican |
| 2012/0323181 A1 | 12/2012 | Shaw et al. |
| 2013/0006194 A1 | 1/2013 | Anderson et al. |
| 2013/0023734 A1 | 1/2013 | Okamura |
| 2013/0030391 A1 | 1/2013 | Baid |
| 2013/0030414 A1 | 1/2013 | Gardner et al. |
| 2013/0053751 A1 | 2/2013 | Holtham |
| 2013/0090607 A1 | 4/2013 | McKinnon et al. |
| 2013/0090608 A1 | 4/2013 | Stout et al. |
| 2013/0090609 A1 | 4/2013 | Sonderegger et al. |
| 2013/0096428 A1 | 4/2013 | Gillies et al. |
| 2013/0121897 A1 | 5/2013 | Davis et al. |
| 2013/0136801 A1 | 5/2013 | Tennican |
| 2013/0138083 A1 | 5/2013 | Tennican |
| 2013/0138085 A1 | 5/2013 | Tennican |
| 2013/0150658 A1 | 6/2013 | Miledi |
| 2013/0178825 A1 | 7/2013 | Helm, Jr. |
| 2013/0184645 A1 | 7/2013 | Baid |
| 2013/0218082 A1 | 8/2013 | Hyer et al. |
| 2013/0237925 A1 | 9/2013 | Trainer et al. |
| 2013/0253443 A1 | 9/2013 | Woehr et al. |
| 2013/0274683 A1 | 10/2013 | Stout et al. |
| 2013/0281972 A1 | 10/2013 | Newby |
| 2013/0296805 A1 | 11/2013 | Erskine |
| 2013/0317426 A1 | 11/2013 | Fiser et al. |
| 2013/0317440 A1 | 11/2013 | Woehr et al. |
| 2014/0018738 A1 | 1/2014 | Steube |
| 2014/0025009 A1 | 1/2014 | Erskine |
| 2014/0039399 A1 | 2/2014 | Burkholz |
| 2014/0046258 A1 | 2/2014 | Stout et al. |
| 2014/0046272 A1 | 2/2014 | Erskine |
| 2014/0052021 A1 | 2/2014 | Burkholz et al. |
| 2014/0052065 A1 | 2/2014 | Woehr et al. |
| 2014/0058329 A1 | 2/2014 | Walker et al. |
| 2014/0072189 A1 | 3/2014 | Jena et al. |
| 2014/0074034 A1 | 3/2014 | Tanabe et al. |
| 2014/0107619 A1 | 4/2014 | Butts et al. |
| 2014/0120168 A1 | 5/2014 | Oldenburg et al. |
| 2014/0128775 A1 | 5/2014 | Andreae et al. |
| 2014/0128820 A1 | 5/2014 | Braga et al. |
| 2014/0135701 A1 | 5/2014 | Woehr et al. |
| 2014/0163470 A1 | 6/2014 | Baid |
| 2014/0187892 A1 | 7/2014 | Gupta et al. |
| 2014/0188002 A1 | 7/2014 | Close et al. |
| 2014/0188003 A1 | 7/2014 | Belson |
| 2014/0200551 A1 | 7/2014 | Glauber |
| 2014/0221931 A1 | 8/2014 | Kuracina et al. |
| 2014/0221932 A1 | 8/2014 | Puhasmagi et al. |
| 2014/0249488 A1 | 9/2014 | Woehr |
| 2014/0257202 A1 | 9/2014 | Woehr |
| 2014/0276458 A1 | 9/2014 | Mansour et al. |
| 2014/0276462 A1 | 9/2014 | Vincent et al. |
| 2014/0288500 A1 | 9/2014 | Leinsing et al. |
| 2014/0296826 A1 | 10/2014 | Finke et al. |
| 2014/0330165 A1 | 11/2014 | Richter et al. |
| 2014/0336583 A1 | 11/2014 | Morrissey et al. |
| 2014/0342461 A1 | 11/2014 | Resh |
| 2014/0357971 A1 | 12/2014 | Eilat et al. |
| 2014/0358115 A1 | 12/2014 | Chelak et al. |
| 2014/0364809 A1 | 12/2014 | Isaacson et al. |
| 2014/0371677 A1 | 12/2014 | Kuracina et al. |
| 2014/0371715 A1 | 12/2014 | Farrell et al. |
| 2015/0005666 A1 | 1/2015 | Terasawa et al. |
| 2015/0005718 A1 | 1/2015 | Walker et al. |
| 2015/0011911 A1* | 1/2015 | Bullington ....... A61B 5/150503 600/575 |
| 2015/0032065 A1 | 1/2015 | Ferguson et al. |
| 2015/0039009 A1 | 2/2015 | Tamano et al. |
| 2015/0073304 A1 | 3/2015 | Millerd |
| 2015/0080801 A1 | 3/2015 | Tanabe et al. |
| 2015/0126932 A1 | 5/2015 | Knutsson |
| 2015/0126933 A1 | 5/2015 | Antonucci |
| 2015/0174374 A1 | 6/2015 | Woehr |
| 2015/0196737 A1 | 7/2015 | Baid |
| 2015/0224267 A1 | 8/2015 | Farrell et al. |
| 2015/0306349 A1 | 10/2015 | Bonnal |
| 2016/0135841 A1 | 5/2016 | Albert et al. |
| 2016/0220161 A1 | 8/2016 | Goral et al. |
| 2016/0220762 A1 | 8/2016 | Goral et al. |

(56) References Cited

U.S. PATENT DOCUMENTS

| | | | |
|---|---|---|---|
| 2016/0220791 A1 | 8/2016 | Akcay et al. | |
| 2016/0220805 A1 | 8/2016 | Goral et al. | |
| 2017/0020428 A1* | 1/2017 | Rogers | A61M 39/04 |
| 2017/0239443 A1* | 8/2017 | Abitabilo | A61M 39/28 |
| 2018/0296149 A1 | 10/2018 | Goral et al. | |
| 2019/0314614 A1 | 10/2019 | Krause et al. | |
| 2019/0314615 A1 | 10/2019 | Johnson et al. | |
| 2019/0357892 A1 | 11/2019 | Abitabilo et al. | |
| 2020/0009366 A1 | 1/2020 | Abitabilo et al. | |

FOREIGN PATENT DOCUMENTS

| | | |
|---|---|---|
| CN | 202223231 U | 5/2012 |
| CN | 102716541 A | 10/2012 |
| CN | 202538063 U | 11/2012 |
| CN | 202605427 U | 12/2012 |
| CN | 202637609 U | 1/2013 |
| CN | 202682524 U | 1/2013 |
| CN | 103007383 A | 4/2013 |
| CN | 203090190 U | 7/2013 |
| DE | 102007044647 A1 | 3/2009 |
| EP | 0451040 A1 | 10/1991 |
| EP | 1107808 A1 | 6/2001 |
| EP | 0868203 B1 | 9/2003 |
| EP | 1011764 B1 | 2/2004 |
| EP | 1469897 A1 | 10/2004 |
| EP | 1349607 B1 | 5/2005 |
| EP | 1292355 B1 | 5/2007 |
| EP | 1804846 B1 | 2/2008 |
| EP | 1716883 B1 | 8/2008 |
| EP | 2044970 A1 | 4/2009 |
| EP | 1864688 B1 | 9/2009 |
| EP | 1958883 B1 | 1/2010 |
| EP | 2204204 A1 | 7/2010 |
| EP | 2450081 A2 | 5/2012 |
| EP | 1448251 B1 | 7/2014 |
| EP | 2764885 A1 | 8/2014 |
| GB | 2508466 B | 10/2014 |
| GB | 2510867 B | 6/2015 |
| IT | RC20050001 A1 | 8/2006 |
| KR | 20080019633 A | 3/2008 |
| SE | 1250635 A1 | 12/2013 |
| WO | WO-8600513 A1 | 1/1986 |
| WO | WO-9632148 A1 | 10/1996 |
| WO | WO-9813083 A1 | 4/1998 |
| WO | WO-9832484 A1 | 7/1998 |
| WO | WO-9844983 A1 | 10/1998 |
| WO | WO-0012160 A1 | 3/2000 |
| WO | WO-0056388 A2 | 9/2000 |
| WO | WO-02051494 A1 | 7/2002 |
| WO | WO-0241932 A3 | 5/2003 |
| WO | WO-03043496 A2 | 5/2003 |
| WO | WO-03061735 A1 | 7/2003 |
| WO | WO-2004050138 A2 | 6/2004 |
| WO | WO-2006082607 A1 | 8/2006 |
| WO | WO-2006086849 A1 | 8/2006 |
| WO | WO-2006070358 A3 | 3/2007 |
| WO | WO-2008102382 A1 | 8/2008 |
| WO | WO 2011/162772 A1 | 12/2011 |
| WO | WO-2012014017 A1 | 2/2012 |
| WO | WO-2012014018 A1 | 2/2012 |
| WO | WO-2012036916 A1 | 3/2012 |
| WO | WO-2012042202 A2 | 4/2012 |
| WO | WO-2012110040 A1 | 8/2012 |
| WO | WO-2013187827 A1 | 12/2013 |
| WO | WO-2014029018 A1 | 2/2014 |
| WO | WO-2014097110 A1 | 6/2014 |
| WO | WO-2014119988 A1 | 8/2014 |
| WO | WO-2014143220 A1 | 9/2014 |
| WO | WO-2014144416 A1 | 9/2014 |
| WO | WO-2014162377 A1 | 10/2014 |
| WO | WO-2015023358 A1 | 2/2015 |
| WO | WO-2015056148 A1 | 4/2015 |
| WO | WO-2015123689 A1 | 8/2015 |
| WO | WO-2017029374 A1 | 2/2017 |
| WO | WO-2019079719 A1 | 4/2019 |

OTHER PUBLICATIONS

Application and File history for U.S. Appl. No. 15/012,059, filed Feb. 1, 2016. Inventors: Goral et al.
Application and File History for Design U.S. Appl. No. 29/582,452, filed Oct. 27, 2016, inventors Chheda et al.
Application and File History for U.S. Appl. No. 15/011,981, filed Feb. 1, 2016, inventors Goral et al.
Application and File History for U.S. Appl. No. 29/581,199, filed Oct. 17, 2016, InventorsAkcay, et al.
BD Nexiva Closed IV Catheter System Product configurations and specifications, 2017, 2 pages.
Examination Report for Australian Application No. 2016211195, dated Jun. 22, 2018, 2 pages.
Extended European Search Report for Application No. 16744268.0, mailed on Aug. 7, 2018, 7 pages.
Extended European Search Report for Application No. 16744275.5, dated Jul. 19, 2018, 7 pages.
ICU Medical, IV Consumables Brochure, 2018, 9 pages.
International Preliminary Report on Patentability for Application No. PCT/US2016/015972, mailed on Aug. 10, 2017, 10 pages.
International Preliminary Report on Patentability for Application No. PCT/US2016/015975, mailed on Aug. 10, 2017, 8 pages.
International Search Report and Written Opinion for Application No. PCT/US2016/015965, mailed on Jun. 8, 2016, 11 pages.
International Search Report and Written Opinion for Application No. PCT/US2016/015972, mailed on May 17, 2016, 14 pages.
International Search Report and Written Opinion for Application No. PCT/US2016/015975, mailed on May 17, 2016, 11 pages.
International Search Report and Written Opinion for Application No. PCT/US2017/018350, mailed on Jun. 2, 2017, 11 pages.
International Search Report and Written Opinion for Application No. PCT/US2016/015958, mailed on Jun. 1, 2016, 12 pages.
International Search Report for corresponding International Application No. PCT/US2017/033478 mailed on Aug. 29, 2017, 6 pages.
Notice of Acceptance for Australian Application No. 2016211195, dated Jul. 1, 2019, 3 pages.
Office Action dated Apr. 7, 2020, for Chinese Application No. 201680008123.7, 12 pages.
Office Action dated Sep. 3, 2019, for Chinese Application No. 201680008123.7, 16 pages.
Search Report and Written Opinion dated Feb. 1, 2019 for PCT Application No. PCT/US2018/056711, 12 pages.
Search Report and Written Opinion dated Jul. 22, 2019 for PCT Application No. PCT/US2019/026469, 16 pages.
Search Report and Written Opinion dated Jul. 23, 2019 for PCT Application No. PCT/US2019/026467, 11 pages.
Search Report dated Oct. 16, 2017 for PCT Application No. PCT/US2017/040887, 4 pages.
Supplementary European Search Report for European Application No. EP17753917.8, dated Jan. 3, 2020, 7 pages.
Tipromed, Safety closed I.V. catheter system, Nov. 10, 2011, 3 pages.
Written Opinion dated Oct. 16, 2017 for PCT Application No. PCT/US2017/040887, 7 pages.
Written Opinion of the International Searching Authority for corresponding International Application No. PCT/US2017/033478, mailed on Aug. 29, 2017, 4 pages.
Search Report dated Dec. 17, 2019 for Application No. PCT/US2019/035978, 16 pages.

* cited by examiner

BLOOD SEQUESTRATION DEVICE AND METHOD

RELATED APPLICATIONS

This application is a divisional of application Ser. No. 16/451,445, filed Jun. 25, 2019, which is a continuation of application Ser. No. 16/434,284 filed Jun. 7, 2019, which claims the benefit of U.S. Provisional Application No. 62/682,362 filed Jun. 8, 2018, each of which is hereby incorporated herein in its entirety by reference.

TECHNICAL FIELD

The present disclosure relates generally to a device for accessing the bloodstream of a patient, and more particularly to a device and method for inhibiting potentially contaminated blood from inclusion in a blood culture test sample.

BACKGROUND

A blood culture is the standard test used to detect microbial infections that may be spreading through a patient's bloodstream. The results from a blood culture are used to verify whether or not an infection is present, and, if so, what type (or types) of microorganisms are responsible for the infection. For example, blood cultures can be used to identify the causative microorganisms in severe pneumonia, puerperal fever, pelvic inflammatory disease, neonatal eppiglottitis, sepsis, and fever of unknown origin.

During a blood culture, a sample of blood (typically at least 10 mL) is with withdrawn from the patient, often via peripheral venipuncture, and stored in one or more blood culture bottles with a specific media for aerobic and anaerobic organisms. Often more than one sample is taken from different areas of the patient's body to form a blood culture set. The proper collection of blood samples is a critical part of conducting a blood culture. An improper collection procedure, for example from improper or incomplete disinfection of the skin area in or around the venipuncture site or coring of skin containing microorganisms by the needle during insertion, can result in a contaminated blood sample.

It is estimated that of the millions of blood culture tests performed on patients each year, roughly one-third of the test results indicate the false presence of microorganisms in the patient's bloodstream (i.e., a false positive). That is, even though microorganisms are found in the patient's blood during the test, those microorganisms were mixed with the blood during the venipuncture procedure. As most caregivers presume that the blood collection procedure was performed correctly, clinicians often treat all positive blood cultures (false or not) with antibiotics. On top of increased patient anxiety and the risks associated with overtreatment, as typical antibiotic treatments range from $4,500 to $10,000, it is estimated that false positive blood cultures significantly add to the cost of healthcare.

Although various strategies and devices have been implemented to decrease blood culture contamination rates, to this day the estimated number of false positive blood cultures remains quite high. Applicants of the present disclosure have identified a need for a blood sampling device and method to address this concern.

SUMMARY OF THE DISCLOSURE

Embodiments of the present disclosure provide a device and method configured to isolate an initial (and potentially contaminated) portion of a blood sample before delivering a balance of the blood sample to an evacuated tube or syringe for use in blood culture testing. In some embodiments, an initial quantity of at least 0.15 mL of blood is sequestered in a manner that enables the remaining flow of blood to be diverted to a blood collection device. In some embodiments, the disclosed device passively diverts the remaining flow of blood after the initial quantity of blood has been sequestered with no moving parts. In some embodiments, the disclosed device can be actively shifted between an initial blood sequestration position and a blood collection position. In some embodiments, a sharp distal tip of the disclosed device can be automatically retracted to a safe position to inhibit unwanted needle sticks.

One embodiment of the present disclosure provides a blood sequestration device configured to isolate an initial, potentially contaminated portion of blood from a flow of blood from vasculature of a patient, prior to directing the flow of blood to an outlet support where the blood can be accessed. The blood sequestration device can include a body member having an interior wall defining a generally "Y" shaped fluid conduit having a distal portion, a first proximal portion, and a second proximal portion. The first proximal portion can define an inlet port configured to be fluidly coupled to vasculature of the patient. The second proximal portion can define a sequestration chamber configured to isolate an initial portion of blood of a flow of blood, and a vent path configured to enable the escape of gas initially trapped within the sequestration chamber. The first proximal portion can be axially aligned with a longitudinal axis of the distal portion. The second proximal portion can define a fluid path and an outlet port configured to be fluidly coupled to a blood collection device. The second proximal portion can be offset from the longitudinal axis of the distal portion by an oblique angle.

In one embodiment axial alignment of the first proximal portion with the distal portion promotes an initial flow of blood into the sequestration chamber. In one embodiment, the vent path includes a gas permeable membrane configured to enable gas initially trapped within the sequestration chamber to vent from the sequestration chamber as blood fills the sequestration chamber. In one embodiment, the outlet port is initially sealed, thereby trapping gas within the second proximal portion, such that a natural pressure of the trapped gas inhibits a flow of blood into the second proximal portion. In one embodiment, the outlet port can include a needle free connector shiftable from a naturally biased closed position to an open position upon the insertion of a Luer taper. In one embodiment, the flow of blood into the second proximal portion is inhibited via a blood collection device. In one embodiment, the outlet port defines a Luer connector. In one embodiment, the oblique angle between the second proximal portion and the distal portion is configured to enable a smooth flow of blood past an opening into the sequestration chamber and into the second proximal portion. In one embodiment, the sequestration chamber has a volume of at least 0.15 mL. In one embodiment, the device further comprises a portion of flexible tubing in fluid communication with the first proximal portion defining at least a portion of the sequestration chamber.

Another embodiment of the present disclosure provides a blood sequestration device configured to isolate an initial portion of blood from a flow of blood of the patient, prior to directing the flow of blood to an outlet port. The blood sequestration device can include a body member having an interior wall defining a fluid conduit having an inlet port, a vented sequestration chamber, a restricted flow path portion positioned between the inlet port and the vented sequestration chamber, and a side outlet port positioned between the inlet port and the restricted flow path portion. The side outlet port can be initially sealed, such that a flow of blood entering the inlet port can follow a path of least resistance to the vented sequestration chamber, where an initial portion of blood can be isolated at least in part by the restricted flow path portion.

In one embodiment, the restricted flow path portion can be defined by a flow restrictor element positioned within the fluid conduit. In one embodiment the vented sequestration chamber can include a gas permeable membrane configured to enable the gas initially trapped within the vented sequestration chamber to vent from the vented sequestration chamber as the initial portion of blood fills the vented sequestration chamber. In one embodiment, sealing the outlet port can cause a natural pressure of gas trapped in proximity to the outlet port to inhibit a flow of blood into the outlet port. In one embodiment, the outlet port can include a needle free connector shiftable from a naturally biased closed position to an open position upon the insertion of a Luer taper. In one embodiment a flow of blood into the second proximal portion is inhibited via a blood collection device. In one embodiment, the outlet port defines a Luer connector. In one embodiment the vented sequestration chamber has a volume of at least 0.15 mL.

Another embodiment of the present disclosure provides a blood sequestration device configured to isolate an initial portion of blood from a flow of blood of a patient, prior to directing the flow of blood to an outlet port. The blood sequestration device can include a body member and an elastomeric blood control valve. The body member can have an inlet port, a vented sequestration chamber, and an outlet port. The vented sequestration chamber can be configured to isolate an initial portion of blood from the flow of blood while enabling the escape of gas trapped within the vented sequestration chamber. The elastomeric blood control valve can be positioned between the inlet port and the outlet port and can be movable between an initial, closed position, where the elastomeric blood control valve inhibits a flow of blood from the inlet port to the output port, and an open position, where the elastomeric blood control valve permits the flow of blood from the inlet port to the outlet port.

In one embodiment, the vented sequestration chamber includes a gas permeable membrane configured to enable gas initially trapped within the vented sequestration chamber to vent from the vented sequestration chamber as the initial portion of blood fills the vented sequestration chamber. In one embodiment, the vented sequestration chamber is operably coupled to a side port positioned between the inlet port and the outlet port of the body member. In one embodiment, sealing the outlet port causes a natural pressure of gas trapped in proximity to the outlet port to inhibit a flow of blood into the outlet port. In one embodiment, the outlet port defines a Luer connector. In one embodiment the vented sequestration chamber has a volume of at least 0.15 mL.

Another embodiment of the present disclosure provides a blood sequestration device configured to automatically retract and safely house a sharpened distal tip of the needle following the isolation of an initial portion of blood and collection of a subsequent sample of blood from a flow of blood of the patient. The blood sequestration device can include a needle, a sequestration body, a needle housing, and a biasing mechanism. The needle can have a sharpened distal tip, a proximal end, and a wall defining a lumen therebetween. The sequestration body can have an inlet port operably coupled to the proximal end of the needle, a vented sequestration chamber in fluid communication with the lumen of the needle and configured to isolate an initial portion of blood from a flow of blood while enabling escape of gas trapped within the sequestration chamber, and an outlet port configured to be fluidly coupled to a blood collection device for the collection of a subsequent sample of blood from the flow of blood. The needle housing can be configured to selectively house the sharpened distal tip of the needle in a safe position. The biasing mechanism can be positioned between the sequestration body and the needle housing, and can be configured to bias the needle from an initial, blood collection position to the safe position, in which the sharpened distal tip of the needle is housed within the needle housing.

In one embodiment, the sequestration body can include one or more wings. In one embodiment the sequestration body can include a guide lock, and the needle housing can define a channel in which the guide lock is configured to traverse. In one embodiment, the guide lock is configured to selectively lock the sequestration body relative to the needle housing against the bias of the biasing mechanism in the blood collection position. In one embodiment, rotation of the sequestration body relative to the needle housing enables automatic withdrawal of the sharpened distal tip of the needle into the needle housing.

Another embodiment of the present disclosure provides a blood sequestration device configured to automatically retract and safely house a sharpened distal tip of the needle following the isolation of an initial portion of blood and collection of a subsequent sample of blood from a flow of blood of a patient. The blood sequestration device can include a housing, needle, needle biasing mechanism, and movable element. The needle can be operably coupled to the housing, and can include a sharpened distal tip, proximal end, and wall defining a lumen therebetween. The needle biasing mechanism can be operably coupled to the proximal end of the needle and can be configured to bias the needle from an initial position, in which the sharpened distal tip of the needle protrudes from the housing, to a safe position, in which the sharpened distal tip of the needle is housed within the housing. The movable element can be shiftable within the housing between an initial blood sequestration position, a blood collection position, and a needle retraction position. The movable element can define a sequestration chamber, a fluid conduit for blood collection, and a chamber configured to retain the needle in the safe position.

In one embodiment, the movable element can define one or more push tabs configured to protrude from the housing to enable user manipulation of the movable element relative to the housing between the initial blood sequestration position, blood collection position, and needle retraction position. In one embodiment, user manipulation of the one or more push tabs in the first direction can cause the movable element to shift from the initial blood sequestration position to the blood collection position. In one embodiment, further user manipulation of the one or more push tabs in the first direction can cause the movable element to shift from the blood collection position to the needle retraction position. In one embodiment, the movable element can define a first push tab and a second push tab configured to protrude from the housing to enable user manipulation of the movable element relative to the housing between the initial blood sequestration position, blood collection position, and needle retraction position. In one embodiment, user manipulation of the first push tab in a first direction causes the movable element to shift from the initial blood sequestration position to the blood collection position. In one embodiment, user manipulation of the second push tab in a second direction causes the movable element to shift from the blood collection position to the needle retraction position. In one embodiment, the sequestration chamber includes a gas permeable membrane configured to enable the gas initially trapped within the sequestration chamber to vent from the sequestration chamber as the initial portion of blood of the flow of blood fills the sequestration chamber. In one embodiment, the fluid conduit for blood collection is operably coupled to a length of flexible tubing configured to be operably coupled to a blood collection device. In one embodiment the fluid conduit for blood collection is occluded upon shifting the movable element to the needle retracted position. In one embodiment, in the needle retracted position, the entire movable element is housed within the housing to inhibit user manipulation of the movable element relative to the housing. In one embodiment, the device further includes a catheter operably coupled to the housing and configured to coaxially ride over the needle for positioning within vasculature of the patient.

Another embodiment of the present disclosure provides a blood sequestration device configured to automatically retract and safely house a sharpened distal tip of a needle following the isolation of an initial portion of blood from a flow of blood from vasculature of the patient. The blood sequestration device can include a housing, needle, needle biasing mechanism, catheter, and movable element. The needle can be operably coupled to the housing, and can include a sharpened distal tip, proximal end, and wall defining a lumen therebetween. The needle biasing mechanism can be operably coupled to the proximal end of the needle and can be configured to bias the needle from an initial position, in which the sharpened distal tip of the needle protrudes from the housing, to a safe position, in which the sharpened distal tip of the needle is housed within the housing. The catheter can be operably coupled to the housing and can be configured to coaxially ride over the needle for positioning within the vasculature of the patient. The movable element can be shiftable within the housing between an initial blood sequestration position and a blood collection position. The movable element can define a sequestration chamber and a chamber configured to retain the needle in the safe position.

In one embodiment, the chamber configured to retain the needle in the safe position can further define a fluid conduit for blood collection. In one embodiment, the fluid conduit for blood collection is operably coupled to a length of flexible tubing configured to be operably coupled to a blood collection device. In one embodiment, the movable element can define one or more push tabs configured to protrude from the housing to enable user manipulation of the movable element relative to the housing between the initial blood sequestration position and the blood collection position. In one embodiment, user manipulation of the one or more push tabs cause the movable element to shift from the initial blood sequestration position to the blood collection position, wherein the needle is retracted into the safe position. In one embodiment, the sequestration chamber includes a gas permeable membrane configured to enable gas initially trapped within the sequestration chamber to vent from the sequestration chamber as the initial portion of blood of the flow of blood fills the sequestration chamber. In one embodiment, in the blood collection position the entire movable element is housed within the housing to inhibit user manipulation of the movable element relative to the housing.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which.

Figures 1A, 1B, 1C:
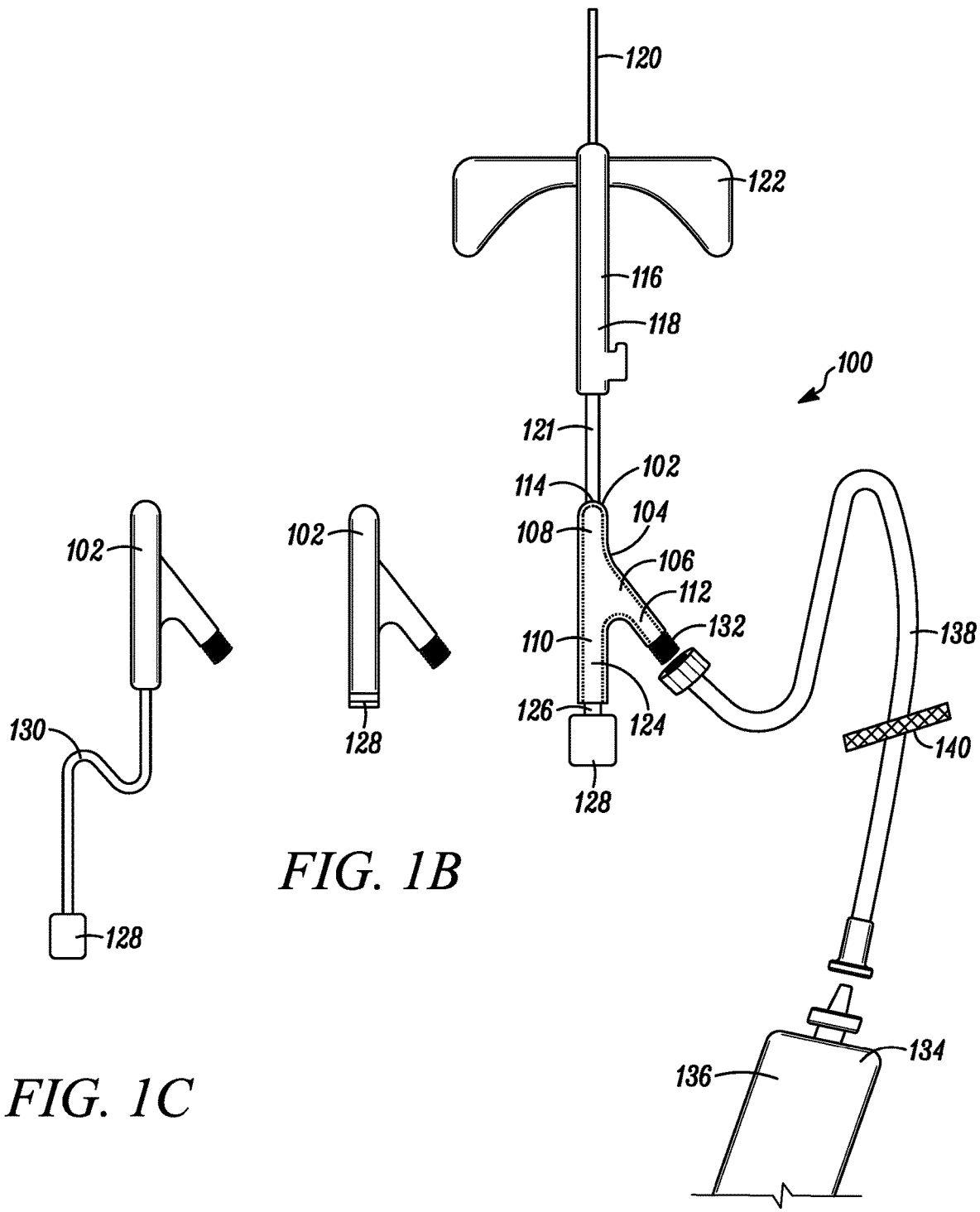
FIG. 1A is a plan view depicting a blood sequestration device in accordance with a first embodiment of the disclosure.
FIG. 1B is a plan view depicting a first alternate body member in accordance with the first embodiment of the disclosure.
FIG. 1C is a plan view depicting a second alternate body member in accordance with the first embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Various blood sequestration devices are described herein for use in accessing the vein of a subject. It is to be appreciated, however, that the example embodiments described herein can alternatively be used to assess the vasculature of a subject at locations other than a vein, including but not limited to the artery of a subject. It is additionally to be appreciated that the term "caregiver,"

"clinician," or "user" refers to any individual that can collect a blood sample for blood culture analysis with any of the example embodiments described herein or alternative combinations thereof. Similarly, the term "patient" or "subject," as used herein is to be understood to refer to an individual or object in which the blood sequestration device is utilized, whether human, animal, or inanimate. Various descriptions are made herein, for the sake of convenience, with respect to the procedures being performed by a clinician to access the vein of the subject, while the disclosure is not limited in this respect.

It is also to be appreciated that the term "distal," as used herein refers to the direction along a longitudinal axis of the blood sequestration device that is closest to the subject during the collection of a blood sample. Conversely, the term "proximal," as used herein, refers to the direction lying along the longitudinal axis of the blood sequestration device that is further away from the subject during the collection of a blood sample, opposite to the distal direction.

Referring to FIG. 1A, a plan view of a blood sequestration device 100 is depicted in accordance with a first embodiment of the disclosure. In one embodiment, the blood sequestration device 100 can include a body member 102 having an interior wall 104 defining a generally "Y" shaped fluid conduit 106. The fluid conduit 106 can include a distal portion 108, a first proximal portion 110, and a second proximal portion 112.

The distal portion 108 can include an inlet port 114 configured to be fluidly coupled to vasculature of a patient. For example, in one embodiment, the inlet port 114 can be in fluid communication with a catheter assembly 116. The catheter assembly 116 can include a catheter hub 118 and a catheter tube 120. In one embodiment, the catheter tube 120 can extend from a tapered distal end to a proximal end, where the catheter tube 120 can be operably coupled to the catheter hub 118. The catheter tube 120 can define a lumen configured to provide a fluid pathway between a vein of the subject and the catheter hub 118. In one embodiment, the catheter tube 120 can include a barium radiopaque line to ease in the identification of the catheter tube 120 during radiology procedures. In an alternative embodiment, the catheter tube 120 can include a metallic radiopaque line, or any other suitable radiopaque material. The catheter hub 118 can include a catheter hub body having a distal end, a proximal end and an internal wall defining an interior cavity therebetween. The interior cavity can include a proximal portion extending from an open proximal end, and a distal portion in proximity to the distal end. In one embodiment, the distal end of the catheter hub body is operably coupled to the proximal end of the catheter tube 120, such that the lumen of the catheter tube is in fluid communication with the proximal portion of the interior cavity.

In some embodiments, the catheter assembly 116 can further include an extension tube 121 operably coupling the catheter assembly 116 to the blood sequestration device 100. In other embodiments, the blood sequestration device 100 can be directly coupled to the catheter assembly 116 and/or the blood sequestration device 100 and the catheter assembly 116 can be formed as a unitary member. Some embodiments of the catheter assembly 116 can further include a wing assembly 122 configured to aid a clinician in gripping, maneuvering and/or securing of the catheter assembly 116 to the patient during the collection of a blood sample.

The first proximal portion 110 can define a sequestration chamber 124 configured to isolate an initial quantity of blood during the collection of a blood sample for blood culture analysis. For example, in one embodiment, blood from the vasculature of the patient under normal pressure can flow into and fill the sequestration chamber 124, thereby displacing a quantity of gas initially trapped within the sequestration chamber 124.

The first proximal portion 110 can include a vent path 126 configured to enable the escape of the gas initially trapped within the sequestration chamber 124, while inhibiting the escape of blood. For example, in one embodiment, the vent path 126 can be sealed at one end by a plug 128. The plug 128 can be made out of an air permeable, hydrophilic material that enables the passage of air, but inhibits the passage of liquid. For example, in one embodiment, the plug 128 can include a plurality of pores shaped and sized to enable the passage of low-pressure gas, but inhibit the passage of low-pressure fluid, such that the pores of the plug 128 become effectively sealed upon contact with the low-pressure fluid. Air that resides within the sequestration chamber 124 is therefore pushed through the plug 128 by the incoming blood, until the blood reaches the plug 128 or is otherwise stopped.

In one embodiment, the plug 128 can be inserted into the vent path 126 (as depicted in FIG. 1A). For example, in one embodiment, the vent path 126 can define a Luer connector configured to accept a portion of the plug 128. In another embodiment, the vent plug 128 can be adhered to the body member 102, so as to occlude the vent path 126 (as depicted in FIG. 1B). Alternatively, the vent plug 128 can be shaped and sized to fit within the first proximal portion 110 of the fluid conduit 106 at a proximal end of the sequestration chamber 124. In yet another embodiment, the plug 128 can be operably coupled to an extension tube 130, which can be operably coupled to the distal end of the first proximal portion, (as depicted in FIG. 1C) such that an interior volume of the extension tubing defines at least a portion of the sequestration chamber, thereby enabling the increase of the internal capacity of the sequestration chamber 124. In one embodiment, the sequestration chamber 124 has a volume of at least 0.15 mL, although other volumes of the sequestration chamber 124 are also contemplated.

In some embodiments, a longitudinal axis of the first proximal portion 110 of the fluid conduit 106 can be axially aligned with a longitudinal axis of the distal portion 108 of the fluid conduit 106. In this manner, the axial alignment of the first proximal portion 110 with the distal portion 108 can promote an initial flow of blood into the sequestration chamber 124.

In some embodiments, the body member 102 of the blood sequestration device 100 can be constructed of a clear or translucent material configured to enable a clinician to view the presence of blood within the sequestration chamber 124. In this respect, the clinician can monitor the proper isolation of an initial portion of blood during the collection of a blood sample for blood culture analysis.

The second proximal portion 112 can define a fluid path and an outlet port 132 configured to be fluidly coupled to a blood collection device 134. For example, in one embodiment, the outlet port 132 can define a Luer connector configured to accept a portion of the blood collection device 134. In other embodiments, the outlet port 132 can define a threaded portion configured to be threadably coupled to a portion of the blood collection device 134.

In some embodiments, the blood collection device 134 can be a vial or syringe 136 fluidly coupled to the outlet port 132 by an extension tube 138. In some embodiments, the flow of blood into the second proximal portion 112 can be inhibited by the blood collection device 134. For example, in one embodiment, the blood collection device 134 can include a clamp 140 configured to occlude the extension tube 138 and/or inhibit the venting of an initial quantity of gas present in the second proximal portion 112 and portions of the blood collection device 134, such that a natural pressure of the trapped gas within the second proximal portion 112 inhibits a flow of blood into the second proximal portion 112.

In some embodiments, a longitudinal axis of the second proximal portion 112 of the fluid conduit 106 can be at an oblique angle to a longitudinal axis of the distal portion 108 of the fluid conduit 106. In this manner, the oblique angle of the second proximal portion 110 can enable a smooth flow of blood past an opening into the sequestration chamber 124 and into the second proximal portion 112, once the sequestration chamber 124 has been filled with the initial quantity of blood for isolation.

Figure 2B:
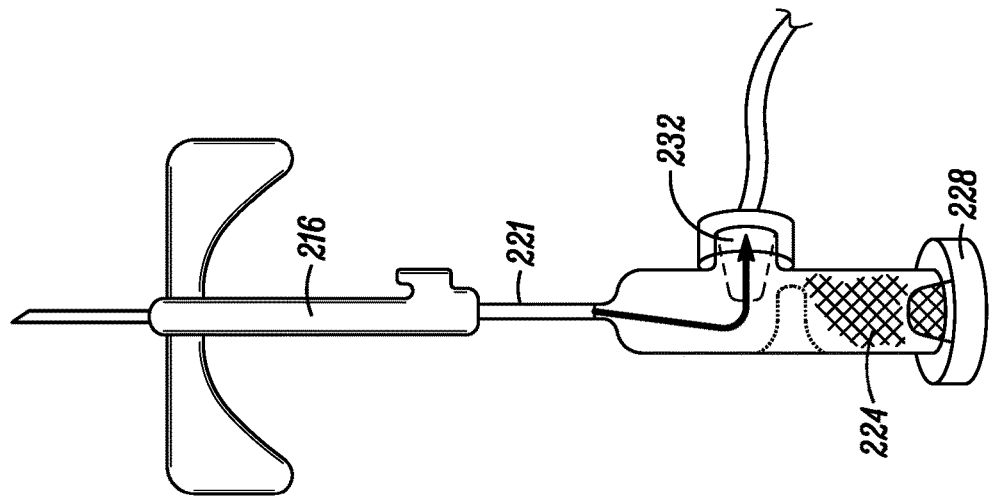
FIGS. 2A-B are plan views depicting a blood sequestration device in accordance with a second embodiment of the disclosure.
Figure 2A:
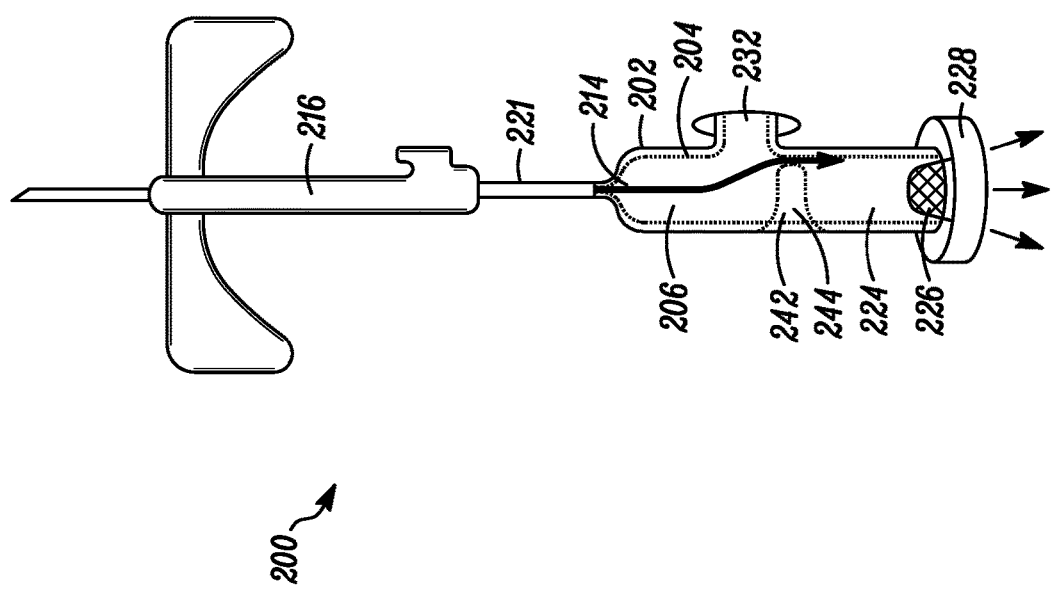

Referring to FIGS. 2A-B, a blood sequestration device 200 is depicted in accordance with a second embodiment of the disclosure. The blood sequestration device 200 can include a body member 202 having an interior wall 204 defining a fluid conduit 206. The fluid conduit 206 can define an inlet port 214, a vented sequestration chamber 224, and an outlet port 232.

The inlet port 214 can be configured to be fluidly coupled to vasculature of a patient. For example, in one embodiment, the inlet port 214 can be in fluid communication with a catheter assembly 216. In some embodiments, the blood sequestration device 200 can be operably coupled to the catheter assembly 216 by an extension tube 221. In other embodiments, the blood sequestration device 200 can be directly coupled to the catheter assembly 216 and/or the blood sequestration device 200 and the catheter assembly 216 can be formed as a unitary member. Some embodiments of the catheter assembly 216 can further include a wing assembly configured to aid a clinician and gripping, maneuvering, and/or securing of the catheter assembly to the patient during the collection of a blood sample.

The vented sequestration chamber 224 can be configured to isolate an initial quantity of blood during the collection of a blood sample. For example, in one embodiment, blood from the vasculature of the patient under normal pressure can flow into and fill the vented sequestration chamber 224, thereby displacing a quantity of gas initially trapped within the sequestration chamber 224. The vented sequestration chamber 224 can include a vent path 226 sealed by an air permeable, hydrophilic material plug 228 configured to enable the passage of air, but inhibit the passage of liquid. Accordingly, air that resides within the vented sequestration chamber 224 can be pushed through the plug 228 by the incoming blood, until the blood reaches the plug 228 or is otherwise stopped.

The outlet port 232 can be positioned between the inlet port 214 and the vented sequestration chamber 224. In one embodiment, the outlet port 232 can be positioned on a side wall of the body member 202, substantially orthogonal to a longitudinal axis of the inlet port 214 and/or the sequestration chamber 224.

In some embodiments, the interior wall 204 of the fluid conduit 206 can define a restricted flow path portion 242 configured to aid in the isolation of an initial quantity of blood within the vented sequestration chamber 224. In some embodiments, the restricted flow path portion 242 is defined by contours of the interior wall 204 of the fluid conduit. In other embodiments, the restricted flow path portion 242 is defined by a separate flow restrictor element 244 positioned within the fluid conduit 206 (as depicted in FIGS. 2A-3B).

Figure 3B:
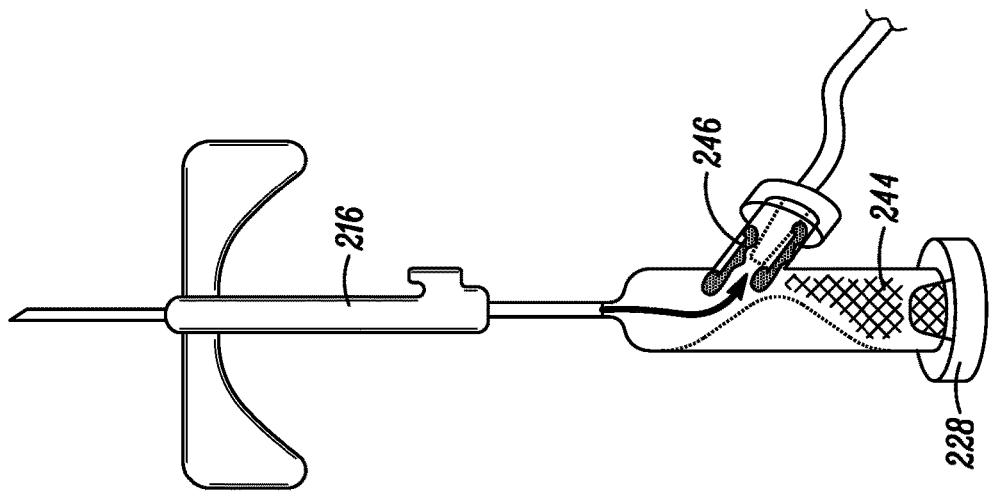
FIGS. 3A-B are plan views depicting a first alternate blood sequestration device in accordance with the second embodiment of the disclosure.
Figure 3A:
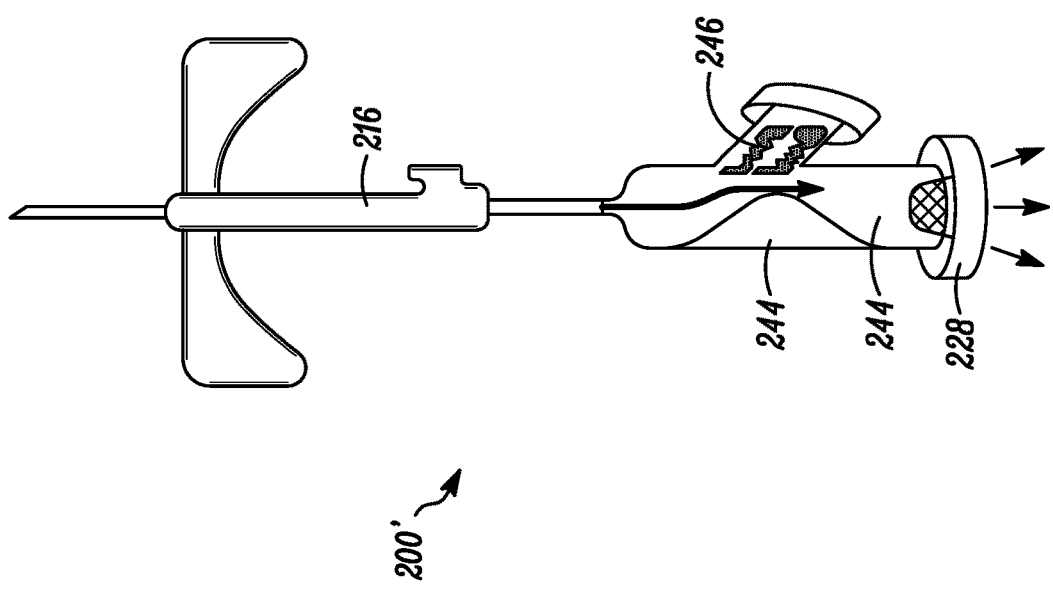

In some embodiments, the outlet port 232 can be initially sealed during the collection of a sample of blood, such that a flow of blood entering the inlet port 214 naturally follows a path of least resistance into the vented sequestration chamber 224, where an initial quantity of blood can be isolated. Accordingly, in one embodiment, sealing of the outlet port 232 causes a natural pressure of gas trapped in proximity to the outlet port 232 to inhibit a flow of blood into the outlet port 232. In one embodiment, the outlet port 232 can define a Luer connector configured to accept a portion of a blood collection device 234. The blood collection device 234 can be configured to occlude the outlet port 232, so as to inhibit the flow of blood into the outlet port 232 and encourage the natural flow of an initial quantity of blood into the vented sequestration chamber 224. In one embodiment, the outlet port 232 can include a needle free connector 246 shiftable from a naturally biased close position to an open position upon the insertion of a Luer taper (as depicted in FIGS. 3A-B).

Figure 4B:
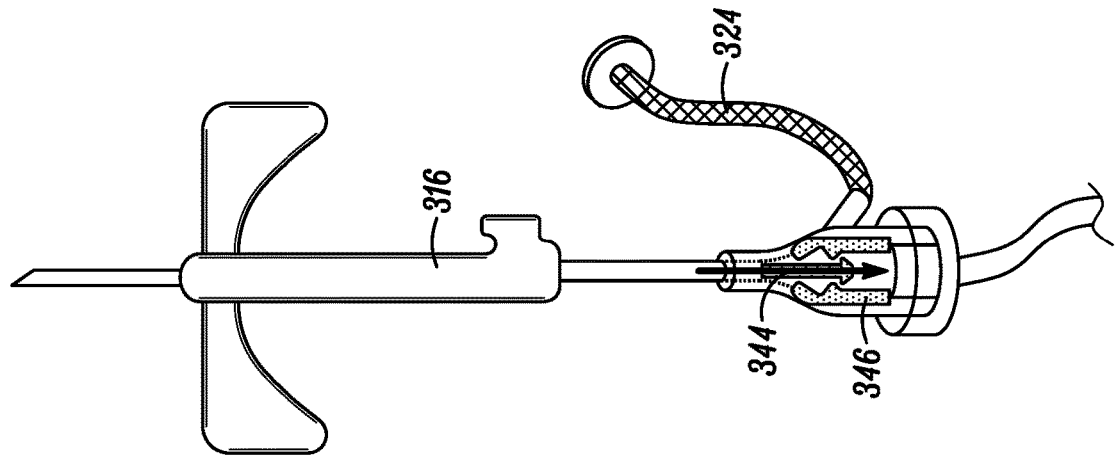
FIGS. 4A-B are plan views depicting a blood sequestration device in accordance with a third embodiment of the disclosure.
Figure 4A:
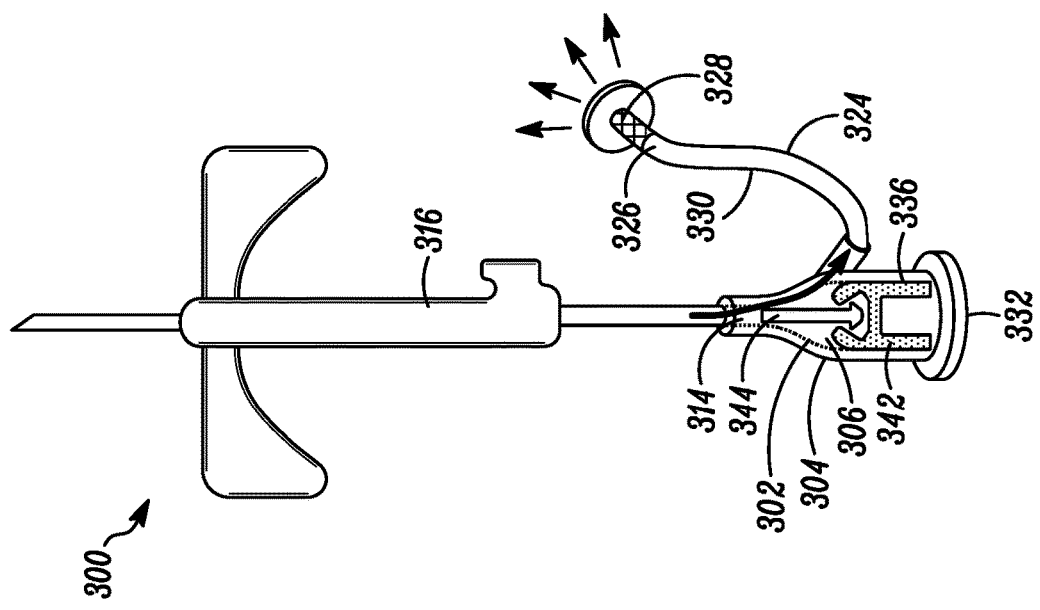

Referring to FIGS. 4A-B, a blood sequestration device 300 is depicted in accordance with a third embodiment of the disclosure. The blood sequestration device 300 can include a body member 302 and an elastomeric blood control valve 342. The body member 302 can include an interior wall 304 defining a fluid conduit 306 having an inlet port 314, a vented sequestration chamber 324, and an outlet port 332.

The inlet port 314 can be configured to be fluidly coupled to a vein of a patient, so as to enable a flow of blood from vasculature of the patient to flow into the fluid conduit 306 of the blood sequestration device 300. For example, in one embodiment, the inlet port 314 can be fluidly coupled to a catheter assembly 316.

The vented sequestration chamber 324 can be configured to isolate an initial quantity of blood during the collection of a blood sample. For example, in one embodiment, blood from the vasculature of the patient under normal pressure can flow into and fill the vented sequestration chamber 324, thereby displacing a quantity of gas initially trapped within the sequestration chamber 324. The vented sequestration chamber 324 can include a vent path 326 sealed by an air permeable, hydrophilic material plug 328 configured to enable the passage of air, but inhibit the passage of liquid.

In one embodiment, the vented sequestration chamber 324 can be positioned between the inlet port 314 and the outlet port 332. In one embodiment, the vented sequestration chamber 324 can extend from a side wall of the body member 302 at an oblique angle relative to a longitudinal axis of the inlet port 314 and/or the outlet port 332. In another embodiment, the vented sequestration chamber 324 can extend from the side wall of the body member 302 substantially orthogonal to a longitudinal axis of the inlet port 314 and/or outlet port 332. In some embodiments, a portion of the vented sequestration chamber 324 can be defined by a length of flexible hollow tubing 330. In some embodiments, the vented sequestration chamber has a volume of at least 0.15 mL, although other volumes of the vented sequestration chamber 324 are also contemplated.

The elastomeric blood control valve 342 can be positioned between the inlet port 314 and the outlet port 332. The elastomeric blood control valve 342 can be configured to move from an initial, closed position (as depicted in FIG. 4A) to inhibit a flow of blood from the inlet port 314 to the outlet port 332, to an open position (as depicted in FIG. 4B) where the elastomeric blood control valve 342 permits the flow of blood from the inlet port 314 to the outlet port 332. In the initial, closed position a natural pressure of gas trapped in proximity to the outlet port 332 inhibits a flow of blood into the outlet port, such that blood naturally flows into the vented sequestration chamber 324. Upon shifting the blood control valve 342 to the open position, the blood flow will follow the path of least resistance to exit the blood sequestration device 300 at the outlet port 332, to which a blood collection device can be operably coupled. Further, when the blood control valve 342 is in the open position, the blood control valve 342 is arranged such that the vented sequestration chamber 324 is sealed from fluid communication with the fluid conduit 306.

In one embodiment, the elastomeric blood control valve 342 can include an actuator 344 secured to the interior wall 304 of the body member 302, so as to extend axially within the fluid conduit 306. The actuator 344 can be a rigid, hollow member configured to enable fluid to pass therethrough. The elastomeric blood control valve 342 can further include a seal member 346 secured within the fluid conduit 306 of the body member 302 with the aid of the actuator 344, such that the seal member 346 is axially shiftable relative to the actuator 344 between the closed position in which flow of fluid through the blood control valve 342 is inhibited or restricted, and the open position, in which the seal member 346 is shifted relative to the actuator 344, thereby enabling the flow of fluid from the inlet port 314, through the elastomeric blood control valve 342, and out through the outlet port 332. One example of such a blood control valve is disclosed in U.S. Pat. No. 9,545,495, the contents of which are incorporated by reference herein.

Figure 5A:
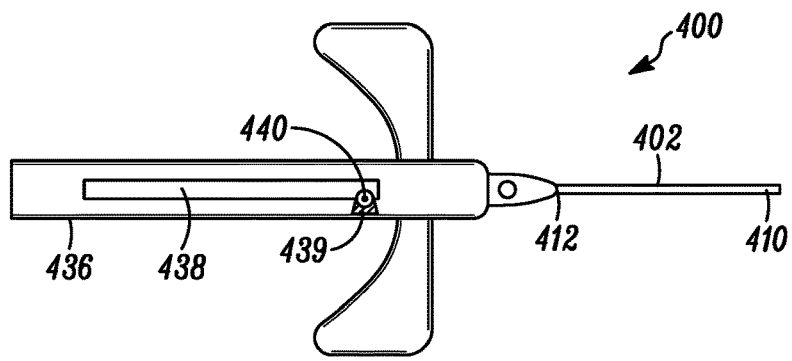
FIG. 5A is a plan view depicting a blood sequestration device in accordance with a fourth embodiment of the disclosure.
Figure 5B:
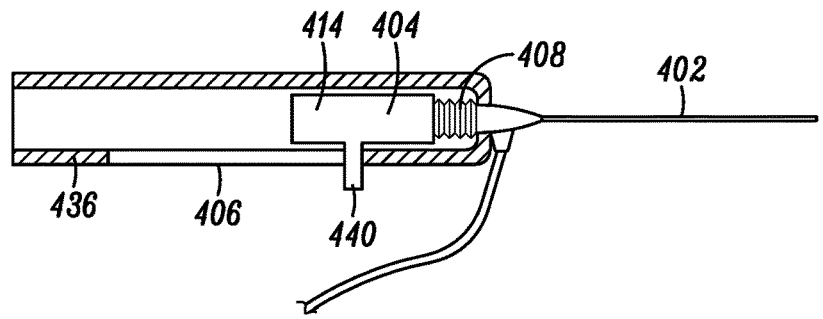
FIG. 5B is a cross-sectional view depicting the blood sequestration device of FIG. 5A.
Figure 5C:
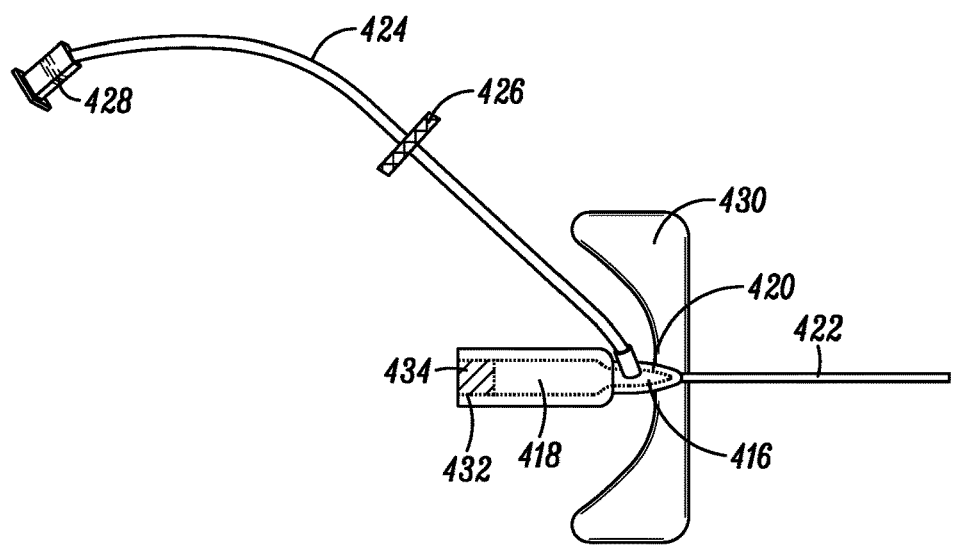
FIG. 5C is a partial cross sectional view depicting a catheter and blood sequestration chamber of a blood sequestration device in accordance with the fourth embodiment of the disclosure.

Referring to FIGS. 5A-C, a blood sequestration device 400 is depicted in accordance with a fourth embodiment of the disclosure. The blood sequestration device 400 can be configured to automatically retract and safely house a sharpened distal tip of the needle following the isolation of an initial quantity of blood during the collection of a blood sample. The blood sequestration device 400 can include a needle 402, a sequestration body 404, a needle housing 406, and a biasing mechanism 408.

The needle 402 can include an elongate cylindrically shaped metal structure defining a lumen that extends between a sharpened distal tip 410 and a proximal end 412. The sharpened distal tip 410 can be constructed and arranged to pierce the skin of the subject during needle insertion. For example, in one embodiment, the sharp distal tip 410 can include a V-point designed to reduce the penetration force used to penetrate the needle 402 and a portion of the sequestration body 404 through the skin, tissue, and vein wall of a subject. In one embodiment, the length of the needle 402 can be extended to aid in accessing vasculature of obese patients.

The proximal end 412 of the needle 402 can be operably coupled to a needle hub 414. In some embodiments, the needle 402 and needle hub 414 can be collectively referred to as a needle assembly. In one embodiment, the needle hub 414 can be constructed to provide a visual indication of a flashback when the sharpened distal tip 410 of the needle 402 enters the vein of the subject. For example, in one embodiment, the needle hub 414 can define a flash chamber in communication with the lumen of the needle 402.

The sequestration body 404 can coaxially ride over at least a portion of the needle 402. In one embodiment, the sequestration body 404 can include a catheter portion 416 and a sequestration chamber 418. The catheter portion 416 can include a catheter hub 420 and a catheter tube 422. The catheter tube can extend from a distal taper end to a proximal end, where the catheter tube 422 can be operably coupled to the catheter hub 420. The catheter tube 422 can define a lumen configured to provide a fluid pathway between a vein of the subject and the catheter hub 420. In one embodiment, the catheter tube 422 can include a barium radiopaque line to ease in the identification of the catheter tube 422 during radiology procedures.

The catheter hub 420 can include a catheter hub body having a distal end, a proximal end, and an internal wall defining an interior cavity therebetween. The interior cavity can include a proximal portion extending from an open proximal end, and a distal portion in proximity to the distal end. In one embodiment, the distal end of the catheter hub body can be operably coupled to the proximal end of the catheter tube 422, such that the lumen of the catheter tube is in fluid communication with the proximal portion of the interior cavity.

In some embodiments, the catheter portion 416 can further comprise a closed catheter assembly, including an extension tube 424, an extension tube clamp 426, and a needleless connector 428. Alternatively, the interior wall defining the interior cavity of the catheter hub 420 can further define a side port (not depicted) configured to enable an alternative fluid communication path with the interior cavity of the catheter hub 420. In one embodiment, the side port can be positioned substantially orthogonal to a longitudinal axis of the catheter hub 420. The side port can be selectively sealed by a flexible sealing member position within the interior cavity of the catheter hub 420. Some embodiments can further include a wing assembly 430 configured to aid a clinician and gripping, maneuvering and/or securing the sequestration body 404 to the subject during the collection of a blood sample.

The sequestration chamber 418 can be configured to isolate an initial quantity of blood during the collection of a blood sample. In one embodiment, the sequestration chamber 418 can have a distal end, a proximal end, and an internal wall defining an interior cavity therebetween. The distal end of the sequestration chamber 418 can be operably coupled to the proximal and the catheter hub 420, such that interior cavities of the catheter hub 420 and sequestration chamber 418 are in fluid communication.

The proximal end of the sequestration chamber 418 can define a vent path 432 configured to enable the escape of gas initially trapped within the sequestration chamber 418, while inhibiting the escape of blood. For example, in one embodiment, the vent path 432 can be sealed at one end by a valve or septum 434. In one embodiment, the septum 434 can be configured to enable at least a portion of the needle 402 to pass therethrough during insertion of the catheter tube 422 into the vein of the subject. The septum 434 can be configured to seal upon withdrawal of the needle 402 through the septum 432, thereby inhibiting the leakage of blood after the needle 402 has been withdrawn. In one embodiment, the septum can further be made out of an air permeable, hydrophilic material configured to enable the passage of air, but inhibit the passage of liquid, thereby enabling air that resides within the sequestration chamber 418 to be evacuated through the septum 432 by the incoming initial quantity of blood to be sequestered.

The needle housing 406 can have a distal end, a proximal end, and a housing wall 436 defining a needle housing cavity therebetween. The needle housing cavity can be shaped and sized to accommodate at least a portion of the needle hub 414 there within. The needle hub 414 can be slidably coupled to the needle housing 406 between an initial, blood collection position (as depicted in FIG. 5B), in which at least a portion of the needle 402 extends beyond the needle housing 406, and a safe position, in which the sharpened distal tip 410 of the needle 402 is housed within the needle housing 406.

The biasing mechanism 408 can be operably coupled between the needle hub 414 and the distal end of the needle housing 406, and can be configured to naturally bias the needle hub 414 to the safe position. In one embodiment, the biasing mechanism 408 can be a coil spring, although other biasing mechanisms are also contemplated. The needle housing wall 436 can further define a channel 438 including a blood collection position notch 439, into which a guide lock 440 of the needle hub 414 can extend. In some embodiments, rotation of the needle hub 414 relative to the needle housing 406 about its longitudinal axis can cause the guide lock 440 to rotate out of the blood collection position notch 439, such that the natural bias of the biasing mechanism 408 can shift the needle hub 414 to the safe position, wherein the needle hub 414 is guided by the guide lock 440 of the needle hub 414 to traverse along a length of the channel 438.

Referring to FIGS. 6A-D, a blood sequestration device 500 is depicted in accordance with a fifth embodiment of the disclosure. The blood sequestration device 500 can be configured to automatically retract and safely house a sharpened distal tip of the needle following the isolation of an initial quantity of blood during the collection of a blood sample. The blood sequestration device 500 can include a housing 502, needle 504, needle biasing mechanism 506, and movable element 508.

Figure 6A:
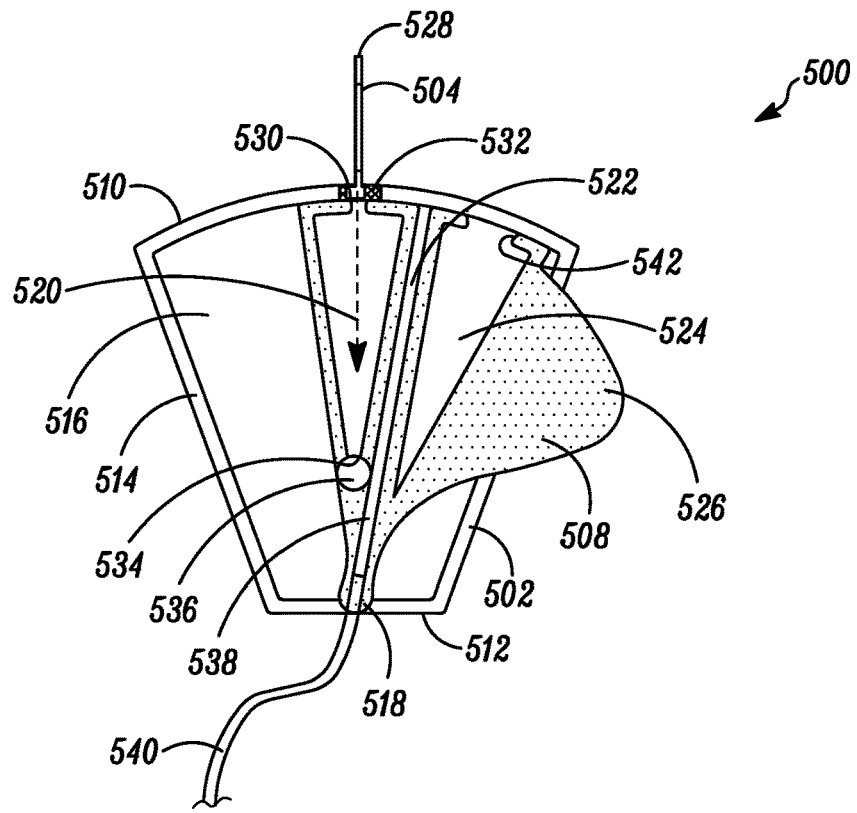
FIGS. 6A-D are plan views a blood sequestration device in accordance with a fifth embodiment of the disclosure.

The housing 502 can have a distal end 510, proximal end 512 and housing wall 514 defining a cavity 516. As depicted in FIG. 6A, in one embodiment, the housing 402 can generally be formed in the shape of a truncated sector, wherein the interior surface of the housing wall 514 along the distal end 510 forms an arc in which points along the interior surface of the housing wall 514 along the distal end 510 are generally equidistant from a point 518 located in proximity to the proximal end 512 of the housing 502.

Figure 6B:
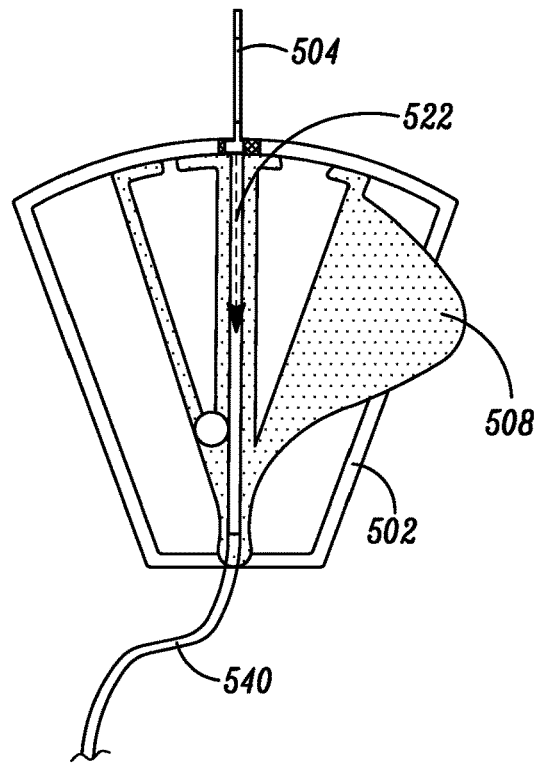
Figure 6C:
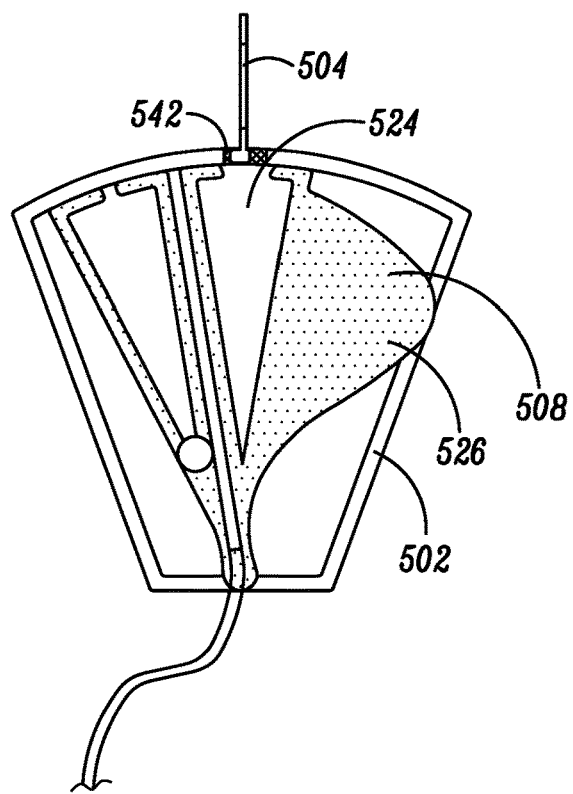
Figure 6D:
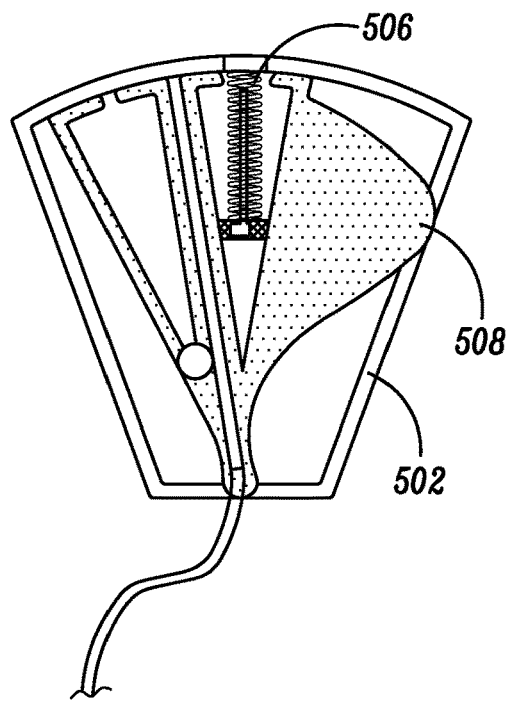

The movable element 508 can reside at least partially within the cavity 516 of the housing 502, and can be pivotably coupled to the housing 502 about point 518, such that the movable element 508 is configured to rotate or shift relative to the housing 502 between an initial blood sequestration position (as depicted in FIG. 6A), a blood collection position (as depicted in FIG. 6B), and a needle retraction position (as depicted in FIG. 6C-D).

In one embodiment, the movable element 508 can define one or more chambers and/or fluid pathways. For example, in one embodiment, the movable element 508 can define a sequestration chamber 520, a blood collection pathway 522, and a chamber 524 configured to house at least a portion of the needle 504 upon retraction. In one embodiment, the movable element 508 can further define one or more push tabs 526 configured to protrude from the housing 502 to enable a clinician to manipulate the movable element 508 relative to the housing 502 between the initial blood sequestration position, blood collection position, and needle retraction position.

The needle 504 can include an elongate cylindrical shaped metal structure defining a lumen that extends between a sharpened distal tip 528 and a proximal end 530. The sharpened distal tip 528 can be constructed and arranged to pierce the skin of the subject during needle insertion. The proximal end 530 of the needle 504 can be operably coupled to a needle hub 532. In some embodiments, the needle 504 and the needle hub 532 can be collectively referred to as a needle assembly.

The needle hub 532 can be slidably coupled to the housing 502 between an initial position (as depicted in FIG. 6A), in which at least a portion of the needle 504 extends beyond the housing 502, and a safe position (as depicted in FIG. 6D), in which the sharpened distal tip 528 of the needle 504 is housed within the housing 502. The biasing mechanism 506 can be operably coupled between the needle hub 532 and the distal end of the housing 502, and can be configured to naturally bias the needle hub 532 to the safe position.

In one embodiment, the blood sequestration device 500 can be provided in the initial blood sequestration position, with the needle 504 extending outwardly from the distal end 510 of the housing 502. Upon insertion of the needle 504 into the vein of a subject, blood flows through the lumen of the needle 504, and into the sequestration chamber 520 defined in the movable element 508.

The sequestration chamber 520 can include a vent path 534 configured to enable the escape of gas initially trapped within the sequestration chamber 520, while inhibiting the escape of blood. For example, in one embodiment, the vent path 534 can be sealed by a plug 536, constructed of an air permeable, hydrophilic material that enables the passage of air, but inhibits the passage of liquid. Air that resides within the sequestration chamber 520 is therefore pushed through the plug 536 by the incoming blood, until the blood reaches the plug 536 or is otherwise stopped. In one embodiment, the sequestration chamber 520 has a volume of at least 0.15 mL, although other volumes of the sequestration chamber 520 are also contemplated.

Once an initial quantity of blood has been sequestered within the sequestration chamber 520, a clinician can manipulate the one or more push tabs 526 to cause the movable element 508 to shift from the initial blood sequestration position to the blood collection position. In the blood collection position, blood can flow from the vein of the subject through the lumen of the needle 504, through the blood collection pathway 522 defined within the movable element 508, and out of the housing 502 through an outlet port 538, which can be operably coupled to a blood collection device via an extension tube 540.

Once a satisfactory quantity of blood has been collected, a clinician can manipulate the one or more push tabs 526 to cause the movable element 508 to shift from the blood sequestration position to the needle retraction position. Prior to movement of the movable element 508 to the needle retraction position, a distal surface of the movable element 508 can inhibit retraction of the needle 504 into the cavity 516 of the housing 502. By contrast, the chamber 524 configured to house at least a portion of the needle 502 upon retraction can include structure defining an opening 542 shaped and sized to enable the needle hub 532 to pass therethrough, thereby enabling the needle 504 to be retracted within the chamber 524 under the natural bias of the needle biasing mechanism 506 to the safe position. In the safe position, the sharpened distal tip 528 of the needle 504 is housed within the chamber 524 to reduce the risk of unintended needle sticks.

In some embodiments, movement of the movable element 508 to the needle retraction position can cause the one or more push tabs to be shifted into the cavity 506 of the housing 502, thereby inhibiting a clinician from further movement of the movable element 508. In one embodiment, movement of the movable element to the needle retraction position can cause a portion of the movable element 508 and/or housing 502 to crimp the extension tube 540, thereby inhibiting leakage of fluid from an attached blood collection device.

In embodiments, the shift between the initial sequestration position (as depicted in FIG. 6A) and the blood collection position (as depicted in FIG. 6B), and the shift from the blood collection position (as depicted in FIG. 6B) to the needle retraction position (as depicted in FIGS. 6C-D) can occur as one fluid motion. In alternative embodiments, an interference protrusion may be introduced within the distal end 510, and within the rotation path of the movable element 508, such that the clinician is aware, via tactile feedback, that the movable element 508 is in the blood collection position and a pause is warranted. In yet other embodiments, a ratchet mechanism can be introduced into pivoting point 518 such that the movable element 508 ceases movement in the blood collection position and the clinician must manipulate the one or more push tabs 526 again to move the movable element 508 from the blood collection position to the needle retraction position.

Referring to FIGS. 7A-D, in some embodiments, the blood sequestration device 500' can include a first push tab 526A and a second push tab 526B configured to protrude from the housing 502 to enable a clinician to manipulate the movable element 508 relative to the housing 502 between the initial blood sequestration position, blood collection position, and needle retraction position. In one embodiment, manipulation of the first push tab 526A in a first direction causes the movable element 508 to shift from the initial blood sequestration position to the blood collection position. Manipulation of the second push tab 526B in a second direction causes the movable element 508 to shift from the blood collection position to the needle retraction position. Other configurations of push tabs 526 defined by the movable element 508 are also contemplated.

Figure 7A:
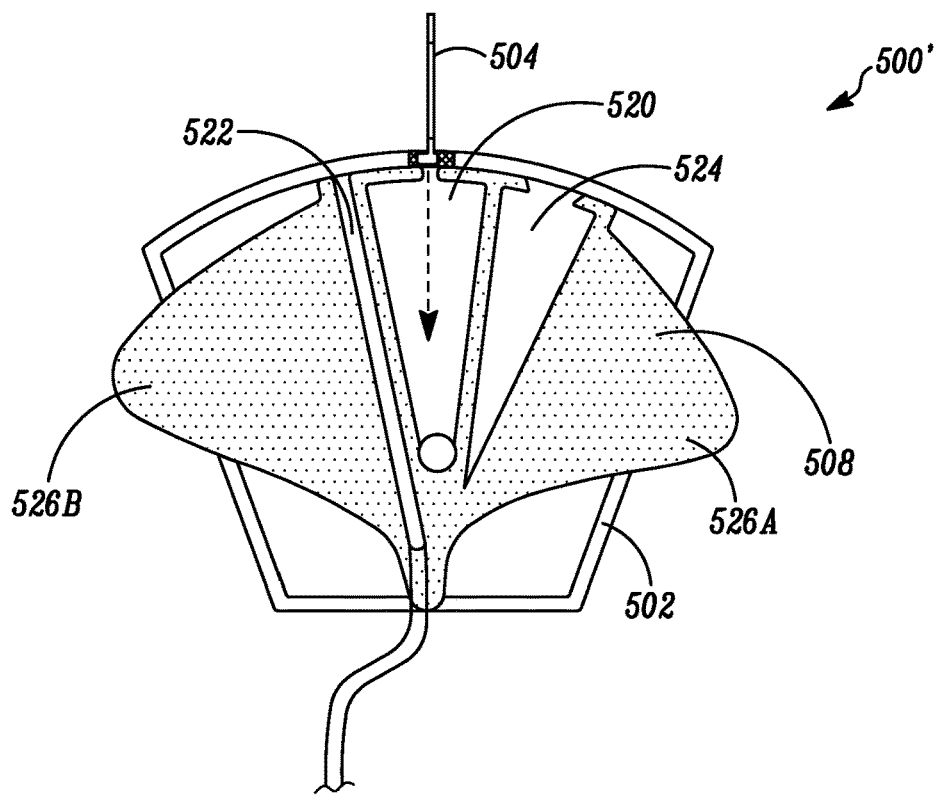
FIGS. 7A-D are plan views depicting an alternate movable element having a pair of push tabs in accordance with the fifth embodiment of the disclosure.
Figure 7B:
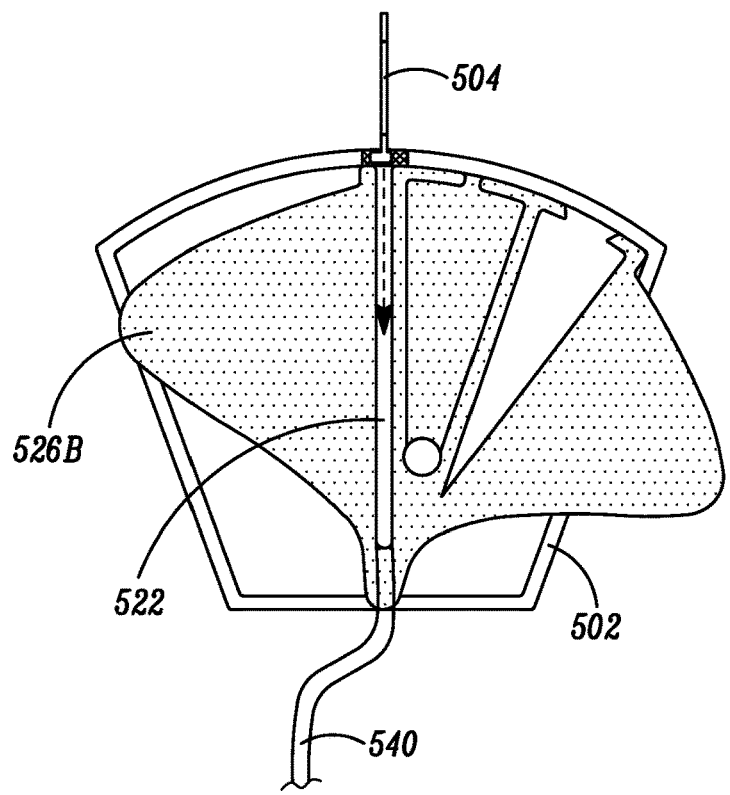
Figure 7C:
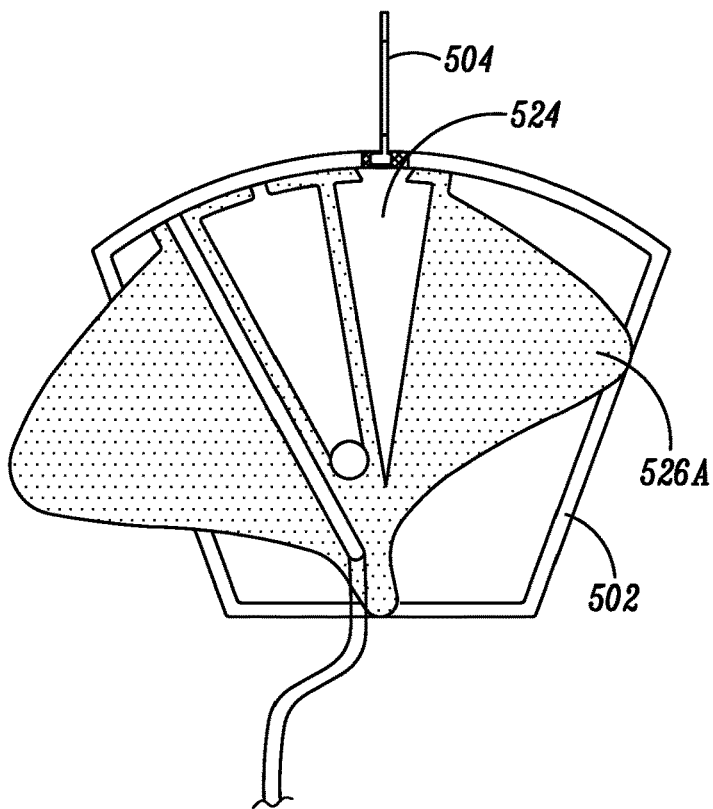
Figure 7D:
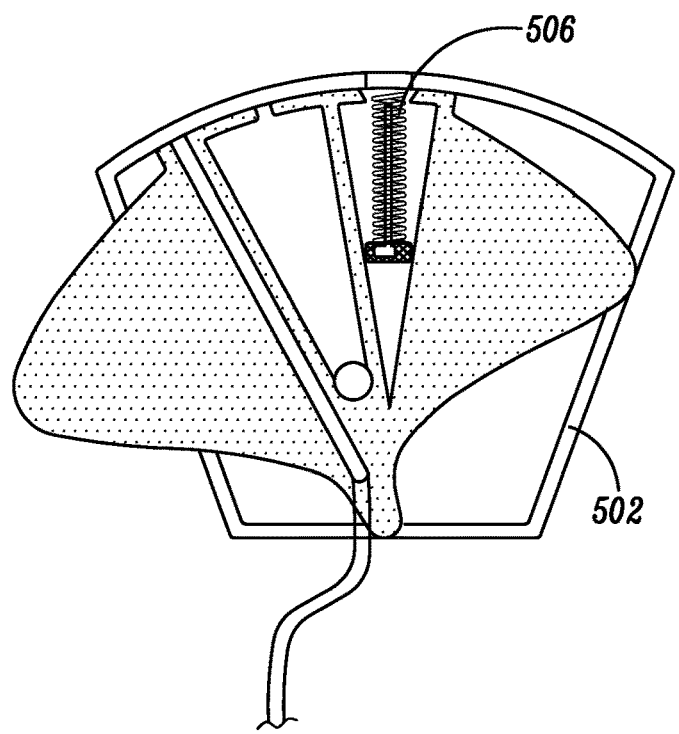

In embodiments, the shift between the initial sequestration position (as depicted in FIG. 7A) and the blood collection position (as depicted in FIG. 7B), and the shift from the blood collection position (as depicted in FIG. 7B) to the needle retraction position (as depicted in FIGS. 7C-D) can occur separately as fluid motions. In alternative embodiments, an interference protrusion may be introduced within the distal end, and within the rotation path of the movable element 508, such that the clinician is aware, via tactile feedback, that the movable element 508 is in the blood collection position and a pause is warranted. In yet other embodiments, a ratchet mechanism can be introduced into the pivoting point such that the movable element 508 ceases movement in the blood collection position and the clinician must manipulate the one or more push tabs 526A again to move the movable element 508 from the blood collection position to the needle retraction position, but bypassing the initial sequestration position.

In some embodiments, the blood sequestration device can further include a catheter assembly to aid in the collection of a blood sample. Referring to FIGS. 8A-D, a blood sequestration device 600 is depicted in accordance with a sixth embodiment of the disclosure. The blood sequestration device 600 can be configured to automatically retract and safely house a sharpened distal tip of a needle following the insertion of a catheter assembly for the collection of a blood sample. The blood sequestration device 600 can include a housing 602, needle 604, needle biasing mechanism 606, movable element 608, and catheter assembly 650.

Figure 8A:
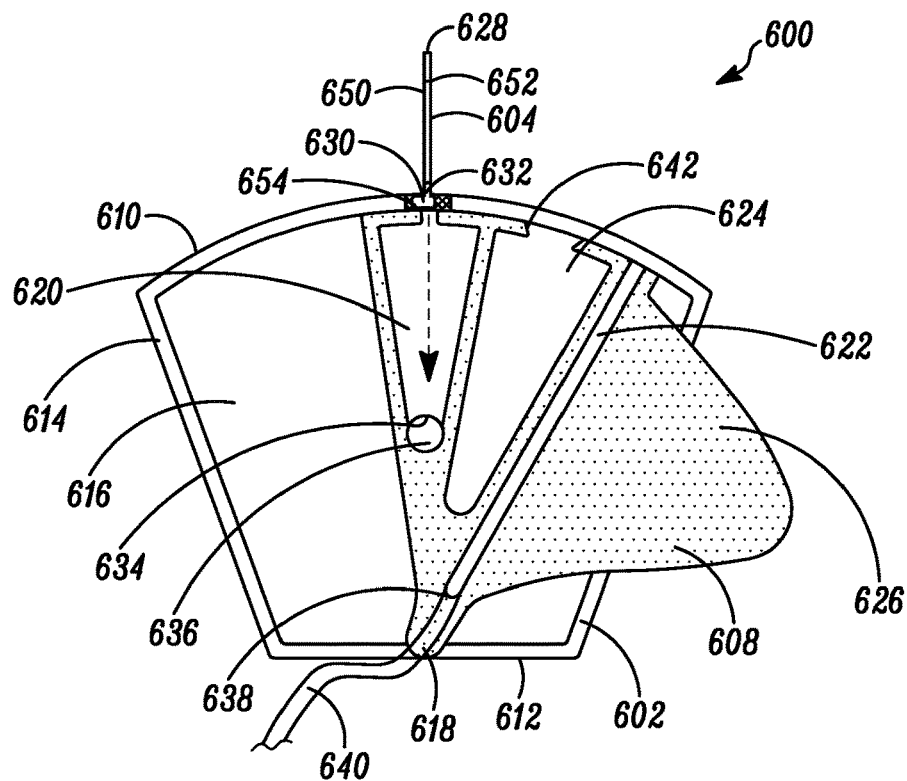
FIG. 8A-D are plan views depicting a blood sequestration device in accordance with a sixth embodiment of the disclosure.

The housing 602 can have a distal end 610, a proximal end 612 and a housing wall 614 defining a cavity 616. As depicted in FIG. 8A, in one embodiment, the housing 602 can generally be formed in the shape of a truncated sector, wherein the interior surface of the housing wall 614 along the distal end 610 forms an arc in which points along the interior surface of the housing wall 614 along the distal end 610 are generally equidistant from a point 618 located in proximity to the proximal end 612 of the housing 602.

Figure 8B:
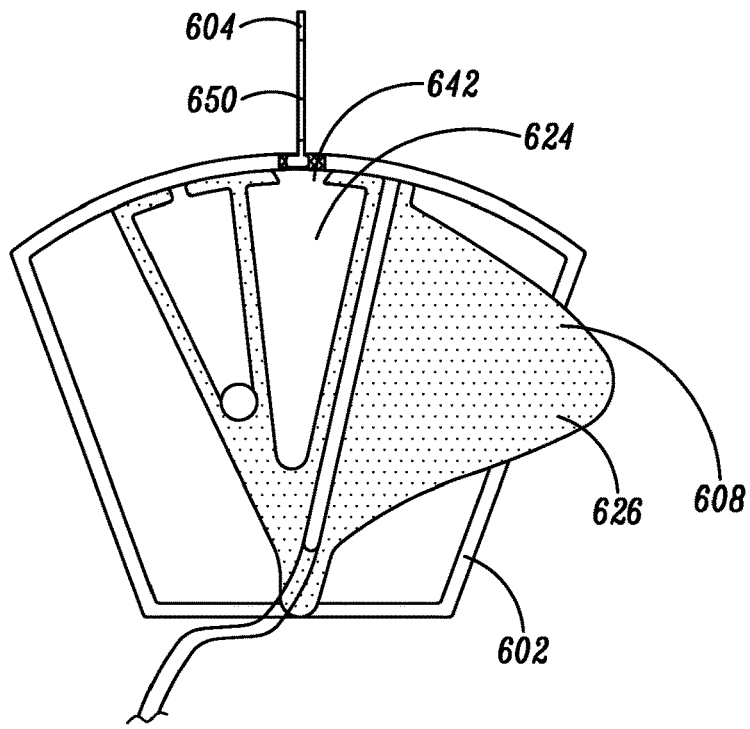
Figure 8C:
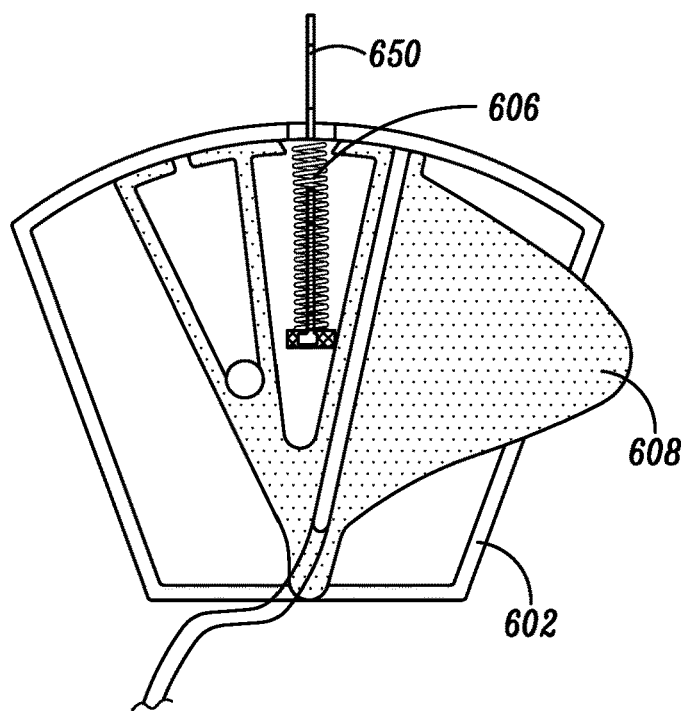
Figure 8D:
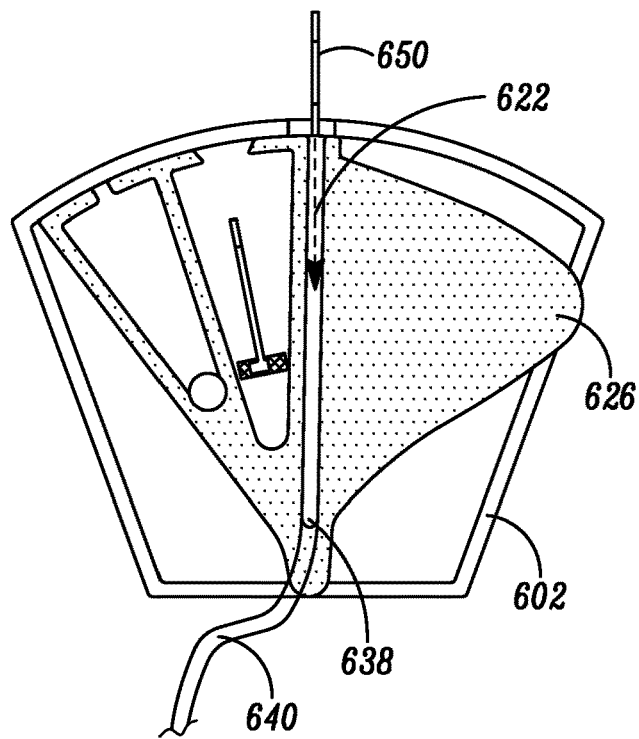

The movable element 608 can reside at least partially within the cavity 616 of the housing 602, and can be pivotably coupled to the housing 602 about a point 618, such that the movable element 608 is configured to rotate or shift relative to the housing 602 between an initial blood sequestration position (as depicted in FIG. 8A), a needle retraction position (as depicted in FIGS. 8B-C), and a blood collection position (as depicted in FIG. 8D).

In one embodiment, the movable element 608 can define one or more chambers and/or fluid pathways. For example, in one embodiment, the movable element 608 can define a sequestration chamber 620, a blood collection pathway 622, and a chamber 624 configured to house at least a portion of the needle 604 upon retraction. In one embodiment, the movable element 608 can further define one or more push tabs 626 configured to protrude from the housing 602 to enable a clinician to manipulate the movable element 608 relative to the housing 602 between the initial blood sequestration position, needle retraction position, and blood collection position.

The needle 604 can include an elongate cylindrical shaped metal structure defining a lumen that extends between a sharpened distal tip 628 and a proximal end 630. The sharpened distal tip 628 can be constructed and arranged to pierce the skin of the subject during needle insertion. The proximal end 630 of the needle 604 can be operably coupled to a needle hub 632. In some embodiments, the needle 604 and needle hub 632 can be collectively referred to as a needle assembly.

The needle hub 632 can be slidably coupled to the housing 602 between an initial position (as depicted in FIG. 8A), in which a least a portion of the needle 604 extends beyond the housing 602, and a safe position (as depicted in FIG. 8C), in which the sharpened distal tip 628 of the needle 604 is housed within the housing 602. The biasing mechanism 606 can be operably coupled between the needle hub 632 and the distal end of the housing 602, and can be configured to naturally bias the needle hub 632 to the safe position.

The catheter assembly 650 can include a catheter tube 652 and a catheter hub 654. The catheter assembly 650 can be configured to coaxially ride over at least a portion of the needle 604 and/or needle assembly. In one embodiment, the catheter hub 654 can be operably coupled to the distal end 610 of the housing 602.

In one embodiment, the blood sequestration device 600 can be provided in the initial blood sequestration position, with the needle 604 and catheter assembly 650 extending outwardly from the distal end 610 of the housing 602. Upon insertion of the needle 604 and catheter tube 652 into the vein of the subject, blood flows through the lumen of the needle 604, and into the sequestration chamber 620 defined within the movable element 608.

The sequestration chamber 620 can include a vent path 634 configured to enable the escape of gas initially trapped within the sequestration chamber 620, while inhibiting the escape of blood. For example, in one embodiment, the vent path 634 can be sealed by a plug 636, constructed of an air permeable, hydrophilic material that enables the passage of air, but inhibits the passage of liquid. Air that resides within the sequestration chamber 620 is therefore pushed through the plug 636 by the incoming blood, until the blood reaches the plug 636 or is otherwise stopped. In one embodiment, the sequestration chamber 620 has a volume of at least 0.15 mL, although other volumes of the sequestration chamber 620 are also contemplated.

Once an initial quantity of blood has been sequestered within the sequestration chamber 620, a clinician can manipulate the one or more push tabs 626 to cause the movable element 608 to shift from the initial blood sequestration position to the needle retraction position. Prior to movement of the movable element 608 to the needle retraction position, a distal surface of the movable element 608 can inhibit retraction of the needle 604 into the cavity 616 of the housing 602. By contrast, the chamber 624, configured to house at least a portion of the needle 604 upon retraction, can include structure defining an opening 642 shaped and sized to enable the needle hub 632 to pass therethrough, thereby enabling the needle 604 to be retracted within the chamber 624 under the natural bias of the needle biasing mechanism 606 to the safe position. In the safe position, the sharpened distal tip 628 of the needle 604 is housed within the chamber 624 to reduce the risk of unintended needle sticks, while leaving the catheter assembly 650 in place within the subject's vein.

Once the needle 604 has been safely retracted, a clinician can manipulate the one or more push tabs 626 to cause the movable element 608 to shift from the needle retraction position to the blood collection position. In the blood collection position, blood can flow from the vein of the subject through the catheter assembly 650, through the blood collection pathway 622 defined within the movable element 608, and out of the housing 602 through an outlet port 638, which can be operably coupled to a blood collection device via an extension tube 640. Once a satisfactory quantity of blood has been collected, a clinician can remove the catheter assembly 650 from the patient's vein.

In embodiments, the shift between the initial sequestration position (as depicted in FIG. 8A) and the needle retraction position (as depicted in FIGS. 8B-C), and the shift from the needle retraction position (as depicted in FIGS. 8B-C) and the blood collection position (as depicted in FIG. 8D) can occur as one fluid motion. In other words, after the initial blood flow is sequestered in the initial sequestration position, the clinician can manipulate the one or more push tabs 626 such that the movable element 608 rotates to the blood collection position, thereby rotating through the needle retraction position. In alternative embodiments, an interference protrusion may be introduced within the distal end, and within the rotation path of the movable element 608, such that the clinician is aware, via tactile feedback, that the movable element 608 is in the needle retraction position and a pause is warranted. In yet other embodiments, a ratchet mechanism can be introduced into pivoting point 618 such that the movable element 608 ceases movement in the needle retraction position and the clinician must manipulate the one or more push tabs 626 again to move the movable element from the needle retraction position to the blood collection position.

Figure 9C:
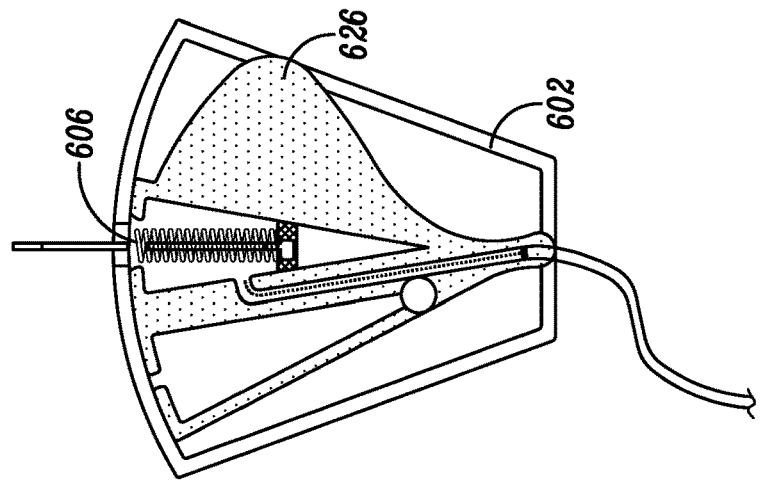
FIGS. 9A-C are plan views depicting an alternate movable element in which the needle retention chamber and blood collection pathway are combined in accordance with the sixth embodiment of the disclosure.
Figure 9B:
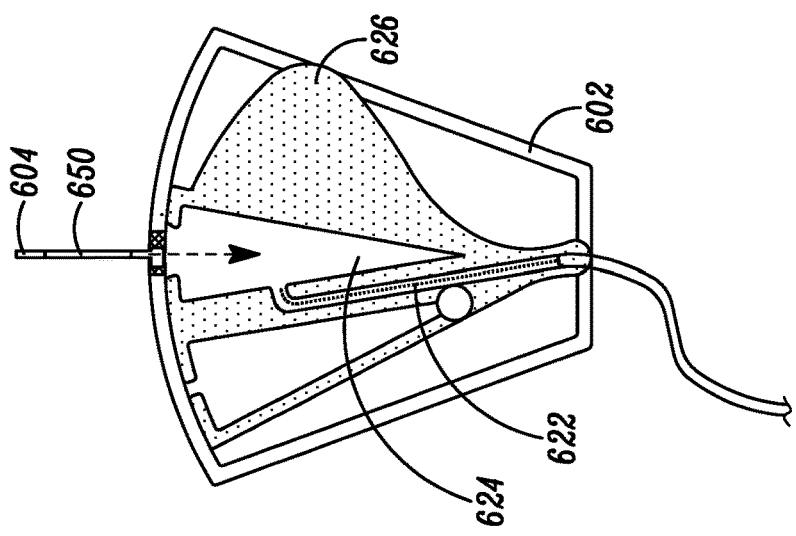
Figure 9A:
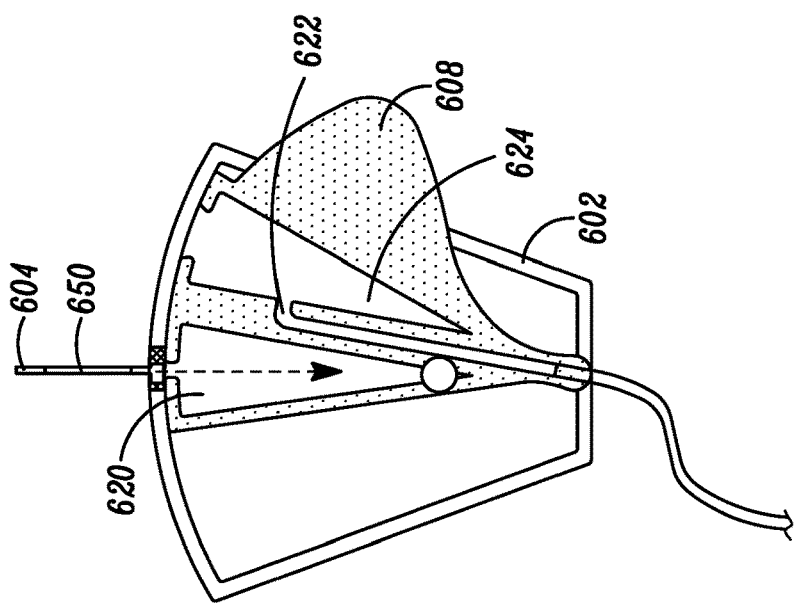

Referring to FIGS. 9A-C, in some embodiments, the blood collection pathway 622 and chamber 624 defined within the movable element 608 can be combined. In this embodiment, once an initial quantity of blood has been sequestered within the sequestration chamber 620, a clinician can manipulate the one or more push tabs 626 to move the movable element 608 to shift from the initial blood sequestration position to the blood collection position, which enables both retraction of the needle 604 within the chamber 624 under the natural bias of the needle biasing mechanism 606 to the safe position, as well as a flow of blood from the vein of the subject through the catheter assembly 650, through the blood collection pathway 622 defined within the movable element 608, and out of the housing 602 through an outlet port 638, which can be operably coupled to a blood collection device. Other configurations of chambers and/or fluid pathways within the movable element 608 are also contemplated.

In embodiments, the shift between the initial sequestration position (as depicted in FIG. 9A) and the blood collection and needle retraction position (as depicted in FIG. 9B-C), can occur freely. In alternative embodiments, an interference protrusion may be introduced within the distal end, and within the rotation path of the movable element 608, such that the moveable element 608 does not easily rotate into the blood collection and needle retraction position, unless the clinician purposefully manipulates the movable element 608 past the tactile feed back of the interference protrusion. In yet other embodiments, a ratchet mechanism can be introduced into the pivoting point such that the movable element 608 ceases movement in the initial sequestration position such that the clinician must manipulate the one or more push tabs 626 through the ratchet mechanism in order to move the movable element 608 from the interference protrusion to the blood collection position and needle retraction position.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. Reference in the specification to "one embodiment," "an embodiment," or "some embodiments" means that a particular feature, structure, or characteristic, described in connection with the embodiment, is included in at least one embodiment of the teaching. Appearances of the phrase "in one embodiment" in various places in the specification are not necessarily all referring to the same embodiment. Moreover, the embodiments described herein are not meant to be an exhaustive presentation of the ways in which the various features of the subject matter hereof may be combined, nor are the embodiments mutually exclusive combinations of features. Rather, the various embodiments can comprise a combination of different individual features selected from different individual embodiments, such that, as understood by persons of ordinary skill in the art, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A blood sequestration device configured to automatically retract and safely house a sharpened distal tip of a needle following isolation of an initial portion of blood and collection of a subsequent sample of blood from a flow of blood of a patient, the blood sequestration device comprising:
    a housing;
    a needle operably coupled to the housing, the needle having the sharpened distal tip, a proximal end and a wall defining a lumen therebetween;
    a needle biasing mechanism operably coupled to the proximal end of the needle and configured to bias the needle from an initial blood sequestration position, in which the sharpened distal tip of the needle protrudes from the housing, to a needle retraction position, in which the sharpened distal tip of the needle is housed within the housing; and
    a movable element rotatable relative to the housing between the initial blood sequestration position, a blood collection position, and the needle retraction position, wherein the movable element defines a sequestration chamber positioned for initial blood sequestration, a fluid conduit positioned for blood collection, and a chamber configured to retain the needle in the needle retraction position, wherein the initial blood sequestration position, the blood collection position, and the needle retraction position are angularly offset from each other.

2. The blood sequestration device of claim 1, wherein the movable element defines one or more push tabs configured to protrude from the housing to enable user manipulation of the movable element relative to the housing among the initial blood sequestration position, the blood collection position, and the needle retraction position.

3. The blood sequestration device of claim 2, wherein the user manipulation of the one or more push tabs in a first direction causes the movable element to rotate from the initial blood sequestration position to the blood collection position.

4. The blood sequestration device of claim 3, wherein further user manipulation of the one or more push tabs in the first direction causes the movable element to rotate from the blood collection position to the needle retraction position.

5. The blood sequestration device of claim 1, wherein the movable element defines a first push tab and a second push tab configured to protrude from the housing to enable user manipulation of the movable element relative to the housing among the initial blood sequestration position, the blood collection position, and the needle retraction position.

6. The blood sequestration device of claim 5, wherein the user manipulation of the first push tab in a first direction causes the movable element to rotate from the initial blood sequestration position to the blood collection position.

7. The blood sequestration device of claim 6, wherein the user manipulation of the second push tab in a second direction causes the movable element to rotate from the blood collection position to the needle retraction position.

8. The blood sequestration device of claim 1, wherein the sequestration chamber includes a gas permeable membrane configured to enable gas initially trapped within the sequestration chamber to vent from the sequestration chamber as the initial portion of blood from the flow of blood fills the sequestration chamber.

9. The blood sequestration device of claim 1, wherein the fluid conduit for blood collection is operably coupled to a length of flexible tubing configured to be operably coupled to a blood collection device.

10. The blood sequestration device of claim 1, wherein the fluid conduit for blood collection is occluded upon rotating the movable element to the needle retraction position.

11. The blood sequestration device of claim 1, wherein in the needle retraction position the entire movable element is housed within the housing to inhibit user manipulation of the movable element relative to the housing.

12. The blood sequestration device of claim 1, further comprising a catheter operably coupled to the housing and configured to coaxially ride over the needle for positioning within vasculature of the patient.

13. A blood sequestration device configured to automatically retract and safely house a sharpened distal tip of a needle following isolation of an initial portion of blood from a flow of blood from vasculature of a patient, the blood sequestration device comprising:
    a housing;
    a needle operably coupled to the housing, the needle having the sharpened distal tip, a proximal end and a wall defining a lumen therebetween;
    a needle biasing mechanism operably coupled to the proximal end of the needle and configured to bias the needle from an initial blood sequestration position, in which the sharpened distal tip of the needle protrudes from the housing, to a needle retraction position, in which the sharpened distal tip of the needle is housed within the housing;
    a catheter operably coupled to the housing and configured to coaxially ride over the needle for positioning within the vasculature of the patient; and
    a movable element rotatable relative to the housing between the initial blood sequestration position and a blood collection position, wherein the movable element defines a sequestration chamber positioned for initial blood sequestration and a chamber configured to retain the needle in the needle retraction position, wherein the initial blood sequestration position and the blood collection position are angularly offset from each other.

14. The blood sequestration device of claim 13, wherein the chamber is configured to retain the needle in the needle retraction position, wherein the chamber further defines a fluid conduit for blood collection.

15. The blood sequestration device of claim 13, wherein the fluid conduit for blood collection is operably coupled to a length of flexible tubing configured to be operably coupled to a blood collection device.

16. The blood sequestration device of claim 13, wherein the movable element defines one or more push tabs configured to protrude from the housing to enable user manipulation of the movable element relative to the housing between the initial blood sequestration position and the blood collection position.

17. The blood sequestration device of claim 13, wherein the user manipulation of the one or more push tabs causes the movable element to rotate from the initial blood sequestration position to the blood collection position, wherein the needle is retracted to the needle retraction position.

18. The blood sequestration device of claim 13, wherein the sequestration chamber includes a gas permeable membrane configured to enable gas initially trapped within the sequestration chamber to vent from the sequestration chamber as the initial portion of blood from the flow of blood fills the sequestration chamber.

19. The blood sequestration device of claim 13, wherein in the blood collection position the entire movable element is housed within the housing to inhibit user manipulation of the movable element relative to the housing.

* * * * *